US008628767B2

(12) United States Patent
Parker et al.

(10) Patent No.: US 8,628,767 B2
(45) Date of Patent: Jan. 14, 2014

(54) PURINE NUCLEOSIDE PHOSPHORYLASE AS ENZYMATIC ACTIVATOR OF NUCLEOSIDE PRODRUGS

(75) Inventors: William B. Parker, Birmingham, AL (US); Eric J. Sorscher, Birmingham, AL (US)

(73) Assignees: The UAB Research Foundation, Birmingham, AL (US); Southern Research Institute, Birmingham, AL (US)

( * ) Notice: Subject to any disclaimer, the term of this patent is extended or adjusted under 35 U.S.C. 154(b) by 0 days.

(21) Appl. No.: 13/059,178

(22) PCT Filed: Aug. 17, 2009

(86) PCT No.: PCT/US2009/054058
§ 371 (c)(1), (2), (4) Date: May 11, 2011

(87) PCT Pub. No.: WO2010/019954
PCT Pub. Date: Feb. 18, 2010

(65) Prior Publication Data
US 2011/0212073 A1 Sep. 1, 2011

Related U.S. Application Data

(60) Provisional application No. 61/089,235, filed on Aug. 15, 2008, provisional application No. 61/225,012, filed on Jul. 13, 2009.

(51) Int. Cl.
*A61K 38/00* (2006.01)
(52) U.S. Cl.
USPC .......................... 424/94.5; 424/94.1; 435/183
(58) Field of Classification Search
None
See application file for complete search history.

(56) References Cited

U.S. PATENT DOCUMENTS

| | | | | |
|---|---|---|---|---|
| 5,552,311 | A | * | 9/1996 | Sorscher et al. ............. 435/348 |
| 6,017,896 | A | * | 1/2000 | Sorscher et al. ............. 514/44 R |
| 6,491,905 | B1 | * | 12/2002 | Sorscher et al. ............. 424/93.2 |
| 6,958,318 | B2 | * | 10/2005 | Sorscher et al. ............. 514/3.7 |

OTHER PUBLICATIONS

Zang et al., J. Biol. Chem., 280:22318-22325 (2005).*
Curiel et al., "High-Efficiency Gene Transfer Mediated by Adenovirus coupled to DNA-Polylysine complexes," Human Gene Therapy, 1992, pp. 147-154, vol. 3.

Debs et al., "Selective Enhancement of Pentamidine Uptake in the Lung by Aerosolization and Delivery in Liposomes," The American Review of Respiratory Disease , 1987, pp. 731-737, vol. 135.
Freireich et al., "Quantitative Comparison of Toxicity of Anticancer Agents in Mouse, Rat, Hamster, Dog, Monkey, and Man," Cancer Chemotherapy Reports, 1966, pp. 219-244, vol. 50.
Gadi et al., "A Long-Acting Suicide Gene Toxin, 6-Methypurine, Inhibits Slow Growing Tumors after a Single Administration," The Journal of Pharmacology and Experimental Therapeutics, 2003, pp. 1280-1284, vol. 304 No. 3.
Ichikawa et al., "Sugar-Modified Nucleosides in Past 10 Years, A Review," Current Medicinal Chemistry, 2001, pp. 385-423, vol. 8 No. 4.
Jiao et al., "Long-term correction of rat model of Parkinson's disease by gene therapy," Nature, 1993, pp. 450-453, vol. 362.
Litzinger et al., "Biodistribution and immunotargetability of ganglioside-stabilized dioleoylphosphatidylethanolamine liposomes," Biochimica et Biophysica Acta, 1992, pp. 179-187, vol. 1104.
Martiniello-Wilks, et al., "Purine nucleoside phosphorylase and fludarabine phosphate gene-directed enzyme prodrug therapy suppresses primary tumour growth and pseudo-metastases in a mouse model of prostate cancer," The Journal of Gene Medicine, 2004, pp. 1343-1357, vol. 6.
Munagala et al., "The Purine Nucleoside Phosphorylase from *Trichomonas vaginalis* Is a Homologue of the Bacterial Enzyme," Biochemistry, 2002, pp. 10382-10389, vol. 41.
Parker et al., "Anti-tumor activity of 2-fluoro-2'-deoxyadenosine against tumors that express *E. coli* purine nucleoside phosphorylase," Cancer Gene Therapy, 2003, pp. 23-29, vol. 10.
Pinnaduwage, et al., "Stable target-sensitive immunoliposomes," Biochemistry, 1992, pp. 2850-2855, vol. 31.
Trubetskoy et al., "Cationic liposomes enhance targeted delivery and expression of exogenous DNA mediated by N-terminal modified poly(l-lysine)-antibody conjugate in mouse lung endothelial cells," Biochimica et Biophysica Acta, 1992, pp. 311-313, vol. 1131.
Weichselbaum et al., "Gene therapy targeted by ionizing radiation," Int. J. Radiation Oncology Biol. Phys., 1992, pp. 565-567, vol. 24.

* cited by examiner

*Primary Examiner* — Blaine Lankford
*Assistant Examiner* — Thomas J Visone
(74) *Attorney, Agent, or Firm* — Blue Filament Law PLLC; Avery N. Goldstein; Marc S. Balban

(57) ABSTRACT

A process for inhibiting a mammalian cancerous cell or virally infected cell includes providing a *Trichomonas vaginalis* purine nucleoside phosphorylase enzyme or a tail mutant purine nucleoside phosphorylase enzyme in proximity to the mammalian cancerous cell or the virally infected cell and exposing the enzyme to a purine nucleoside phosphorylase enzyme cleavable substrate to yield a cytotoxic purine analog. The process includes introducing to the cell a vector containing the phosphorylase enzyme, or a DNA sequence coding for the same and delivering to the cell an effective amount of the substrate such as 9-($\beta$-D-arabinofuranosyl)-2-fluoroadenine (F-araA).

7 Claims, 8 Drawing Sheets

Fig. 7: Tailed mutant PNP encoded in Ad-PNP virus

1. Initiation(ATG) and termination(TAA) codon: boxed
2. wild-type *E.coli* PNP sequence: underlined
3. Bolded GGTAA: GAG TAA in wild-type *E.coli* PNP sequence coding Glu+termination codon(TAA); an A deletion (from 239th codon, glutamic acid) in Ad-PNP resulted in a frame-shift.
4. 30 amino acid tail (Double underlined): 30 amino acid tail added in place of glutamic acid.

```
TCTAGGCGGC CGCGATCTAT ACATTGAATC AATATTCGCA ATTAGCCATA      51
TTAGTCATTG GTTATATAGC ATAAATCAAT ATTGGCTATT GGCCATTGCA     101
TACGTTGTAT CTATATCATA ATATGTACAT TTATATTGGC TCATGTCCAA     151
TATGACCGCC ATGTTGACAT TGATTATTGA CTAGTTATTA ATAGTAATCA     201
ATTACGGGGT CATTAGTTCA TAGCCCATAT ATGGAGTTCC GCGTTACATA     251
ACTTACGGTA AATGGCCCGC CTGGCTGACC GCCCAACGAC CCCCGCCCAT     301
TGACGTCAAT AATGACGTAT GTTCCCATAG TAACGCCAAT AGGGACTTTC     351
CATTGACGTC AATGGGTGGA GTATTTACGG TAAACTGCCC ACTTGGCAGT     401
ACATCAAGTG TATCATATGC CAAGTCCGCC CCCTATTGAC GTCAATGACG     451
GTAAATGGCC CGCCTGGCAT TATGCCCAGT ACATGACCTT ACGGGACTTT     501
CCTACTTGGC AGTACATCTA CGTATTAGTC ATCGCTATTA CCATGGTGAT     551
GCGGTTTTGG CAGTACACCA ATGGGCGTGG ATAGCGGTTT GACTCACGGG     601
GATTTCCAAG TCTCCACCCC ATTGACGTCA ATGGGAGTTT GTTTTGGCAC     651
CAAAATCAAC GGGACTTTCC AAAATGTCGT AATAACCCCG CCCCGTTGAC     701
GCAAATGGGC GGTAGGCGTG TACGGTGGGA GGTCTATATA AGCAGAGCTC     751
GTTTAGTGAA CCGTCAGATC CGGTCGCGCG AATTCGAGCT CGGTACCCGG     801
GGATCCGGTG GTGGTGCAAA TCAAAGAACT GCTCCTCAGT GGATGTTGCC     851
TTTACTTCTA GGCCTGTACG GAAGTGTTAC TTCTGCTCTA AAAGCTGCGG     901
AATTGTACCC GCGGCCGCAT GGCTACCCCA CACATTAATG CAGAAATGGG     951
CGATTTCGCT GACGTAGTTT TGATGCCAGG CGACCCGCTG CGTGCGAAGT    1001
ATATTGCTGA AACTTTCCTT GAAGATGCCC GTGAAGTGAA CAACGTTCGC    1051
GGTATGCTGG GCTTCACCGG TACTTACAAA GGCCGCAAAA TTTCCGTAAT    1101
GGGTCACGGT ATGGGTATCC CGTCCTGCTC CATCTACACC AAAGAACTGA    1151
TCACCGATTT CGGCGTGAAG AAAATTATCC GCGTGGGTTC CTGTGGCGCA    1201
GTTCTGCCGC ACGTAAAACT GCGCGACGTC GTTATCGGTA TGGGTGCCTG    1251
CACCGATTCC AAAGTTAACC GCATCCGTTT TAAAGACCAT GACTTTGCCG    1301
CTATCGCTGA CTTCGACATG GTGCGTAACG CAGTAGATGC AGCTAAAGCA    1351
CTGGGTATTG ATGCTCGCGT GGGTAACCTG TTCTCCGCTG ACCTGTTCTA    1401
CTCTCCGGAC GGCGAAATGT TCGACGTGAT GGAAAAATAC GGCATTCTCG    1451
GCGTGGAAAT GGAAGCGGCT GGTATCTACG GCGTCGCTGC AGAATTTGGC    1501
GCGAAAGCCC TGACCATCTG CACCGTATCT GACCACATCC GCACTCACCA    1551
GCAGACCACT GCCGCTGAGC GTCAGACTAC CTTCAACGAC ATGATCAAAA    1601
TCGCACTGGA ATCCGTTCTG CTGGGCGATA AAGGTAAGCG GCCGCGGGGA    1651
TCCTCTAGAG TCGACCTGCA GGCATGCAAG CTTGGGATCT TGTGAAGGA     1701
ACCTTACTTC TGTGGTGTGA CATAATTGGA CAAACTACCT ACAGAGATTT    1751
AAAGCTCTAA CGTAAATATA AAATTTTTAA GTCTATAATG TGTTAAACTA    1801
CTGATTCTAA TTGTTTGTGT ATTTTAGATT CACAGTCCCA AGGCTCATTT    1851
CAGGCCCCTC AGTCCTCACA CTCTGTTCAT GATCATAATC AGCCATACCA    1901
CATTTGTAGA GGTTTTACTT GCTTTAAAAA ACCTCCCACA CCTCCCCCTG    1951
AACCTGAAAC ATAAAATGAA TGCAATTGTT GTTGTTAACT TGTTTATTGC    2001
AGCTTATAAT GGTTACAAAT AAAGCAATAG CATCACAAAT TTCACAAATA    2051
AAGCATTTTT TTCACTGCAT TCTAGTTGTG GTTTGTCCAA ACTCATCAAT    2101
GTATCTTATC ATGTCTGGAT CGCGGCCGCC TAGA
```

Fig. 8 New PNP amino acid sequence in Ad-PNP

MATPHINAEMGDFADVVLMPGDPLRAKYIAETFLEDAREVNNVRGMLGFTGTYKGRKISVMGHGMGIPSCSIYTKELITDFGVKKIIRV
GSCGAVLPHVKLRDVVTGMGACTDSKVNRIRFKDHDFAAIADFDVVRNAVDAAKALGIDARVGNLFSADLFYSPDGEMFDVMEKYGILG
VEMEAAGIYGVAAEFGAKALTICTVSDHIRTHEQTTAAERQTTFNDMIKIALESVLLGDK**GKRPRGSSRVDLQACKLGIFVKEPYFCGV
T**

Wild-type PNP sequence in black
30 amino acid tail unique in PNP encoded in Ad-PNP virus :Bolded

US 8,628,767 B2

PURINE NUCLEOSIDE PHOSPHORYLASE AS ENZYMATIC ACTIVATOR OF NUCLEOSIDE PRODRUGS

RELATED APPLICATIONS

This application is the U.S. national phase of PCT/US2009/054058 filed Aug. 17, 2009, which claims priority benefit of U.S. Provisional Application Ser. No. 61/089,235 filed Aug. 15, 2008 and U.S. Provisional Application Ser. No. 61/225,012 filed Jul. 13, 2009, the contents of both are incorporated herein by reference in their entirety.

GRANT REFERENCE

The research carried out in connection with this invention was supported in part by grant CA119170 from the National Institutes of Health.

FIELD OF THE INVENTION

The invention relates to a process of using tailed mutants and wild-type *Trichomonas vaginalis* purine nucleoside phosphorylases as an enzymatic activator for prodrug substrates and in particular to prodrug substrates such as 9-(β-D-arabinofuranosyl)-2-fluoroadenine (F-araA, fludarabine) and 2-Cl-2'-deoxyadenosine (Cl-dAdo, cladribine).

BACKGROUND OF THE INVENTION

A prodrug activation strategy for selectively impairing tumor cells involves the expression of a gene encoding an exogenous enzyme in the tumor cells and administration of a substrate for that enzyme. The enzyme acts on the substrate to generate a substance toxic to the targeted tumor cells. This technique has advantages over the expression of directly toxic genes, such as ricin, diphtheria toxin, or *pseudomonas* exotoxin. These advantages include the capability to: 1) titrate cell impairment; 2) optimize therapeutic index by adjusting either levels of prodrug or of recombinant enzyme expression; and 3) interrupt toxicity by omitting administration of the prodrug. In addition, this technique uses prodrugs with different effects on different cell types, allowing treatment to be adjusted according to a specific disease state.

Enzymes useful in a prodrug activation approach have been described and include enzymes such as thymidine kinase, cytosine deaminase and purine nucleoside phosphorylase (PNP), as described in U.S. Pat. Nos. 5,338,678; 5,552,311; 6,017,896 and 6,207,150. However, the effectiveness of tumor treatment using prodrug activation techniques is limited in cases where side effects of substrate administration are present. For example, the prodrug ganciclovir, often used in combination with thymidine kinase, can cause unwanted immunosuppressive effects.

The search for a particular purine nucleoside phosphorylase with cleavage activity for the important chemotherapeutic F-araA has not previously been successful in part due to the large number of PNP candidates that need to be surveyed and the difficulties surrounding isolating and expressing each PNP. Many microorganisms generate PNPs capable of cleaving adenine-containing nucleosides to adenine. To illustrate, there are at least 17 microorganisms alone reported to express PNP including: *Leishmania donovani*; *Trichomonas vaginalis*; *Trypanosoma cruzi*; *Schistosoma mansoni*; *Leishmania tropica*; *Crithidia fasciculata*; *Aspergillis* and *Penicillium*; *Erwinia carotovora*; *Helix pomatia*; *Ophiodon elongates* (lingcod); *E. coli*, *Salmonella typhimurium*; *Bacillus subtilis*; *Clostridium*; *mycoplasma*; *Trypanosoma gambiense*; and *Trypanosoma brucei*.

Thus, there exists a need for a prodrug activation method for treating tumors that improves efficacy and overcomes the problem of side effects.

SUMMARY OF THE INVENTION

A process is provided for inhibiting a cancerous cell by providing a wild-type *Trichomonas vaginalis* purine nucleoside phosphorylase (Tv-PNP) enzyme in proximity to the cancerous cell and exposing the enzyme to a substrate cleaved by the enzyme to yield a cytotoxic purine analog, the substrate being fludarabine, cladribine, analog of cordycepin, analog of 2',3'-dideoxyadenosine, 5'-methyl(talo)-6-methylpurine-riboside, 5'-methyl(talo)-2'-deoxy-6-methylpurine-riboside, 5'-methyl(allo)-6-methylpurine-riboside, 2-F-5'-deoxyadenosine, or 2-F-α-L-lyxo-adenine. The Tv-PNP enzyme is provided by expression in the cancerous cell, or a cell proximal thereto, or is through administration of the enzyme proximal to the target cell. Tailed mutant purine nucleoside phosphorylase (tm-PNP) enzymes derived from various organisms are also provided as novel compositions operative herein for cancer cell inhibition.

A commercial kit is provided for inhibiting a mammalian cancerous cell that includes a Tv-PNP enzyme, a tm-PNP enzyme, or a vector containing a DNA sequence expressible in the cancerous cell and coding for a Tv-PNP enzyme, tm-PNP enzyme, or a combination thereof; and a substrate of fludarabine, cladribine, analog of cordycepin, analog of 2',3'-dideoxyadenosine, 5'-methyl(talo)-6-methyl-purine-riboside, 5'-methyl(talo)-2'-deoxy-6-methylpurine-riboside, 5'-methyl(allo)-6-methylpurine-riboside, 2-F-5'-deoxyadenosine, or 2-F-α-L-lyxo-adenine, or a combination of such substrates.

A composition of target cell lysate, Tv-PNP/tm-PNP and a prodrug that when cleaved by a Tv-PNP/tm-PNP yields a cytotoxic cleavage product purine analog is also provided. This composition is particularly useful in directing subsequent therapies.

BRIEF DESCRIPTION OF THE FIGURES

FIG. 7 is an adenovirus expressible tm-PNP nucleotide sequence mapping relative to a wild-type *E. coli*; and FIG. 8 is a tm-PNP amino acid sequence encoded by the nucleotide sequence of FIG. 7 showing the resulting tail addition.

DETAILED DESCRIPTION OF THE PREFERRED EMBODIMENTS

Figure 1:
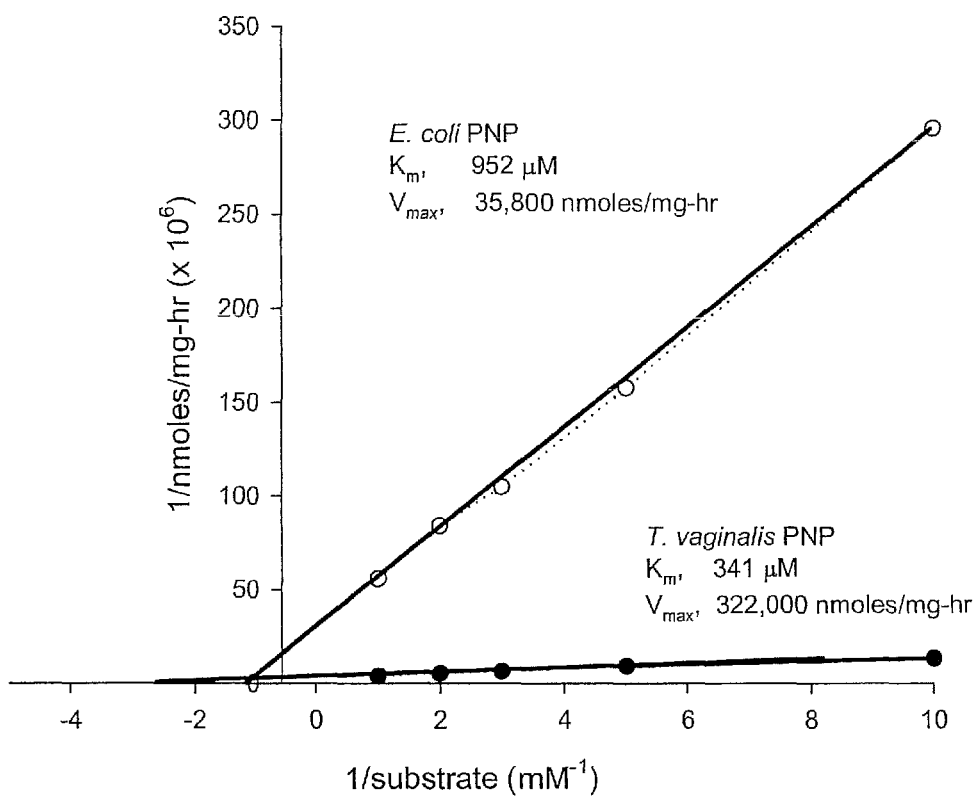
FIG. 1 depicts the kinetic parameters of F-araA with *E. coli* PNP and Tv-PNP.
Figure 2:
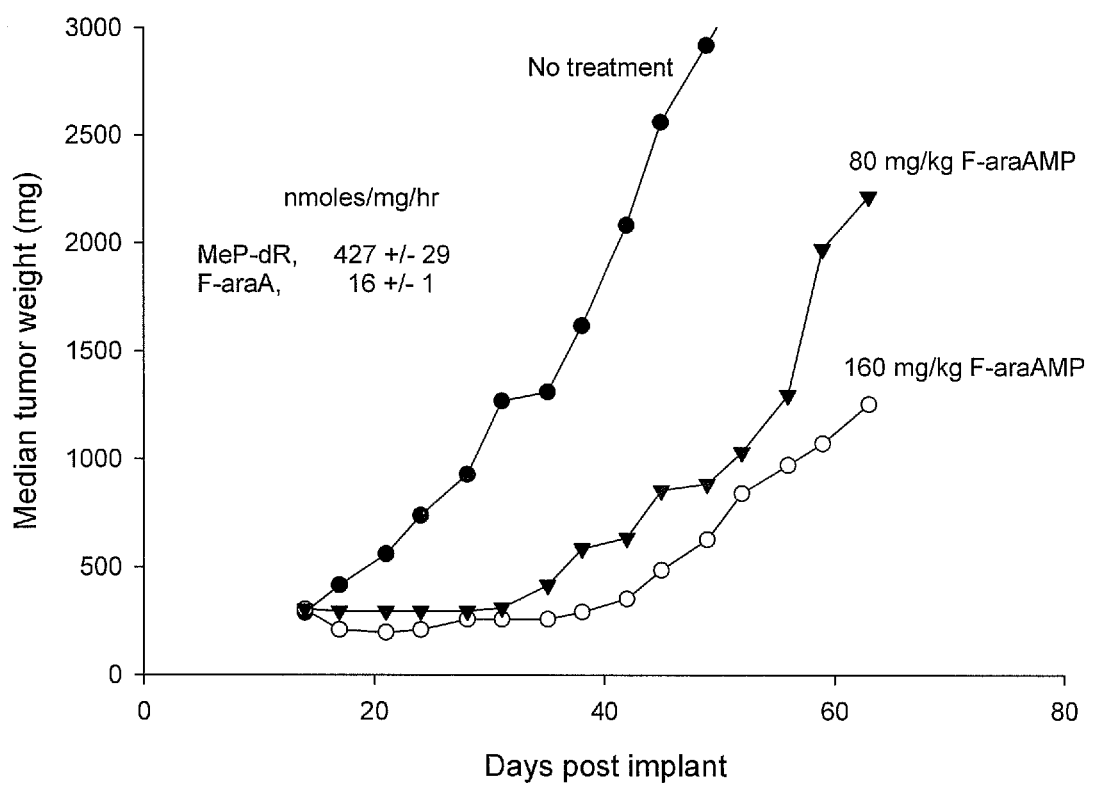
FIG. 2 depicts the effectiveness of F-araAMP (a prodrug or F-araA) against tumor xenographs in mice in which only 10% of the cells express Tv-PNP.

The subject of the present invention is a purine nucleoside phosphorylase isolated from *T. vaginalis*. Purine nucleoside phosphorylases and nucleoside hydrolases are present in diverse organisms illustratively including mammals such as humans, and microorganisms, such as *Leishmania donovani; Trichomonas vaginalis; Trypanosoma cruzi; Schistosoma mansoni; Leishmania tropica; Crithidia fasciculata; Aspergillis* and *Penicillium; Erwinia carotovora; Helix pomatia; Ophiodon elongatus; Salmonella typhimurium; Bacillus subtilis; Clostridium; mycoplasma; Trypanosoma gambiense; Trypanosoma brucei; Sulfolobus solfataricus*; and *E. coli*.

A nucleoside phosphorylase catalyzes the reaction: purine nucleoside+$PO_4$→ribose-1-$PO_4$ (or deoxyribose-1-phosphate)+purine base. The present invention provides nucleotide sequences and amino acid sequences encoding native *Trichomonas vaginalis* purine cleaving enzymes and tm-PNP sequences having surprisingly higher biological activity in cleaving specific substrates compared to structurally related wild-type PNP enzymes from other organisms and the wild-type sequence from which the tailed mutation enzyme is derived, respectively.

The term "biological activity" as used herein is intended to mean a measurement of the amount of end product produced by the reaction of a specified amount of a purine cleavage enzyme in the presence of a substrate in a period of time measured by appropriate method as shown in Example 2.

A compound that is a substrate for the enzyme to produce a cytotoxic purine analog which impairs the metabolism, function, or replication of a cell is referred to herein interchangeably as a "prodrug" or a "substrate."

The term "pathogenic viral infection" as used herein is intended to mean infection by a virus causing disease or pathological effects.

The term "pharmaceutically acceptable" as used herein is intended to mean a material that is not biologically or otherwise undesirable, which can be administered to an individual without causing significant undesirable biological effects or interacting in a deleterious manner with any of the other components of the pharmaceutical composition in which it is contained.

According to the present invention the cleavage of a prodrug by Tv-PNP or tm-PNP yields a cytotoxic purine analog that inhibits a cancerous (or virally infected) target cell. It is appreciated that the cytotoxic purine analog need not be generated within the cancerous cell and instead a bystander effect exists in which the cytotoxic purine analog generated within a tumor cell can travel to neighboring tumor cells and confer their destruction. The concentration of cytotoxic purine analog needed to inhibit a virally infected or cancerous target cell depends on factors including the identity of the cytotoxic purine analog, intercellular fluid exchange rate, rate of cytotoxic purine analog cellular membrane transport, and rates of incorporation into DNA or RNA, and effectiveness as an inhibitor of protein synthesis.

Tv-PNP or tm-PNP is operative to inhibit mammalian cancerous or virally infected target cells in vitro or in vivo and in a human or a non-human subject. Tv-PNP or tm-PNP is delivered in vivo by any of the processes detailed in U.S. Pat. No. 6,958,318 B2 as a substitute for the *E. coli* PNP described therein. These delivery processes illustratively include recombinant viral vectors; *Clostridium, Salmonella* and *E. coli* bacterial vectors; antibody-conjugated liposomes; reintroduction of subject cells genetically modified to express the Tv-PNP or tm-PNP enzyme; lipofection; viruses such as retrovirus, adenovirus, herpes virus, measles virus, adeno-associated virus, or a vacuvirus; and direct injection of the Tv-PNP or tm-PNP enzyme into proximity to the mammalian cancerous cell.

The invention provides a method of at least inhibiting, and typically killing replicating or non-replicating, transfected or transduced mammalian cells and bystander cells through the following steps: (a) transfecting or transducing targeted mammalian cells with a nucleic acid encoding a Tv-PNP or tm-PNP or providing such enzyme directly in proximity to the targeted cells; and (b) contacting the targeted cells expressing or provided with the Tv-PNP cleavage enzyme with a substrate for the enzyme to produce a toxic purine base in quantities greater than that produced by wild-type or substitution *E. coli* PNP and other PNPs thereby killing the targeted cells and also bystander cells not expressing or containing the cleavage enzyme. Thus, in the presence of substrate, the Tv-PNP or tm-PNP cleavage enzyme produces a toxic product. The operation of the invention can occur in vitro or in vivo, with human or non-human mammalian or other cells.

As used herein the term "inhibiting" is an alteration of a normal physiological activity. Specifically, inhibiting is defined as lysing, reducing proliferation, reducing growth, increasing or decreasing the expression or rate of degradation of a gene, RNA, protein, lipid, or other metabolite, inducing apoptosis or other cell death mechanisms, or increasing, decreasing, or otherwise altering the function of a protein or nucleic acid.

In one embodiment of the present invention, the Tv-PNP or tm-PNP enzyme is provided by targeting the enzyme to the cells. More preferably, the Tv-PNP or tm-PNP enzyme is targeted to the cells by conjugating the enzyme to an antibody.

The enzyme may be encoded by a gene provided to the cells. For example, the gene provided to the cells encodes Tv-PNP or tm-PNP and is operably linked to a tyrosinase gene promoter. Alternatively, the gene is provided in a carrier molecule such as polymeric films, gels, microparticles and liposomes.

In another embodiment, the present invention provides a method of at least inhibiting, and typically killing by lysis both replicating or non-replicating targeted mammalian cells and bystander cells. The process includes the steps of: (a) delivering the Tv-PNP or tm-PNP to the targeted mammalian cells; and (b) contacting the targeted cells with an effective amount of a nucleoside substrate for the Tv-PNP or tm-PNP, wherein the substrate is relatively nontoxic to mammalian cells and is cleaved by Tv-PNP or tm-PNP to yield a purine base which is toxic to the targeted mammalian cells and bystander cells in proximity thereto and in a quantity greater than that provided by wild-type or substitution mutant *E. coli* PNP. Representative examples of purine analog substrates include fludarabine, cladribine, analog of cordycepin, analog of 2',3'-dideoxyadenosine, 5'-methyl(talo)-6-methylpurine-riboside, 5'-methyl(talo)-2'-deoxy-6-methylpurine-riboside, 5'-methyl(allo)-6-methylpurine-riboside, 2-F-5'-deoxyadenosine, or 2-F-α-L-lyxo-adenine.

The present invention also provides a composition for killing targeted mammalian cells, inclusive of: (a) a Tv-PNP or tm-PNP enzyme that cleaves a purine nucleoside substrate; and (b) an amount of the purine nucleoside substrate effective to kill the targeted cells when cleaved by the enzyme.

The present invention is also directed to a vector containing a DNA sequence coding for a Tv-PNP or tm-PNP protein where the vector is capable of replication in a host and which includes in operable linkage: a) an origin of replication; b) a promoter; and c) a DNA sequence coding for said Tv-PNP or tm-PNP protein. Preferably, the vector is a retroviral vector, an adenoviral vector, an adeno-associated viral vector, a herpes vector, a vacuvirus, a viral vector, or a plasmid.

The present invention is also directed to a host cell transfected with the vector of the present invention so that the vector expresses a Tv-PNP or tm-PNP protein. Preferably, such host cells are selected from the group consisting of bacterial cells, mammalian cells and insect cells.

It is appreciated in the inventive method that a host cell is optionally transfected or transduced with a vector ex vivo or in vitro and subsequently administered to a patient, preferably at or near a tumor site or location of viral infection. Optionally, a cell is delivered systemically.

Some of the processes and compositions exemplified herein involve transfecting cells with the Tv-PNP or tm-PNP gene and subsequently treating with a comparative nontoxic purine nucleoside prodrug that is converted to a toxic purine analog. A particularly preferred prodrug is F-araA, but it is appreciated that other prodrugs are also operative in the present invention.

Tv-PNP or tm-PNP differs from human PNP in its more efficient acceptance of adenine and certain guanine-containing nucleoside analogs as substrates and is shown herein to be surprisingly effective at cleaving particular substrates compared to structurally similar PNPs of different bacterial and parasitic origins. PNP expressed in tumor cells cleaves the nucleoside, liberating a toxic purine analog. Purine analogs freely diffuse across cell membranes in comparison to nucleoside monophosphates such as those generated using HSV Thd kinase that generally remain inside the cell in which they are formed. A toxic adenine analog formed after conversion by Tv-PNP or tm-PNP can be converted by adenine phosphoribosyl transferase to toxic nucleotides and kill all transfected cells, and diffuse out of the cell and kill surrounding cells that were not transfected (bystander cells).

The inventive composition has utility as a biologically functional system operable to produce destruction such as lytic destruction of a target cancerous or virally infected cell. Illustratively, the inventive composition and method use the enzymatic action of Tv-PNP on a prodrug to yield a cytotoxic purine analog able to transit the cell membrane and cause cell lysis. By way of example, such a composition affords information as to the copy number of Tv-PNP or tm-PNP enzymes present per unit volume, while the molar ratio of prodrug: cytotoxic cleavage product therefrom is indicative of activity kinetics. These assay results are readily obtained by conventional HPLC or other assays. For tumor target cells, these results when coupled with time differentiated tumor mass scans provide invaluable data as to the nature of subsequent treatments with Tv-PNP or tm-PNP, adjunct chemotherapeutic, surgical, or radiation treatment, or a combination thereof.

Transcriptional Regulation of the PNP Encoding Sequence

In a preferred embodiment, Tv-PNP or tm-PNP is encoded on a prokaryotic gene such that the expression of the Tv-PNP or tm-PNP in mammalian cells is achieved by the presence of a eukaryotic transcriptional regulatory sequence linked to the PNP-encoding sequences. The Tv-PNP or tm-PNP gene can illustratively be expressed under the control of strong constitutive promoter/enhancer elements that are obtained within commercial plasmids (for example, the SV40 early promoter/enhancer (pSVK30 Pharmacia, Piscataway, N.J.), Moloney murine sarcoma virus long terminal repeat (pBPV, Pharmacia), mouse mammary tumor virus long terminal repeat (pMSG, Pharmacia), and the cytomegalovirus early promoter/enhancer (pCMVβ, Clontech, Palo Alto, Calif.).

Selected populations of cells can also be targeted for inhibition or destruction by using genetic transcription regulatory sequences that restrict expression of the Tv-PNP or tm-PNP coding sequence to certain cell types, a strategy that is referred to as transcription targeting. A candidate regulatory sequence for transcription targeting preferably fulfills two important criteria as established by experimentation: (i) the regulatory sequence directs enough gene expression to result in the production of enzyme in therapeutic amounts in targeted cells, and (ii) the regulatory sequence does not direct the production of sufficient amounts of enzyme in non-targeted cells to impair the therapeutic approach. In this form of targeting the regulatory sequences are functionally linked with the Tv-PNP sequences to produce a gene that is activated only in those cells that express the gene from which the regulatory sequences were derived. Regulatory sequences that have been shown to fulfill the criteria for transcription targeting in gene therapy include regulatory sequences from the secretory leucoprotease inhibitor, surfactant protein A, and α-fetoprotein genes. A variation on this strategy is to utilize regulatory sequences that confer "inducibility" so that local administration of the inducer leads to local gene expression. As one example of this strategy, radiation-induced sequences have been described and advocated for gene therapy applications (Weichselbaum, et al., *Int. J. Radiation Oncology Biol. Phys.*, 24:565-567 (1992)) and are operative herein.

Tissue-specific enhancer/promoters are operative in directing Tv-PNP or tm-PNP expression, and thereby Tv-PNP- or tm-PNP-mediated toxicity, to specific tissues. For example, human tyrosinase genetic regulatory sequences are sufficient to direct Tv-PNP or tm-PNP toxicity to malignant melanoma cells. Mouse tyrosinase sequences from the 5-prime flanking region (−769 bp from the transcriptional start site) of the gene are capable of directing reporter gene expression to malignant melanoma cells. Although the mouse and human tyrosinase sequences in the 5-prime flanking region are similar, Shibata et al., *Journal of Biological Chemistry*, 267:20584-20588 (1992) showed that the human 5-prime flanking sequences in the same region used by Vile and Hart (−616 bp from the transcriptional start site) did not confer tissue specific expression. Although Shibata et al. suggested that the 5-prime flanking region would not be useful to target gene expression to tyrosinase expressing cells (melanomas or melanocytes), a slightly different upstream fragment from that used by Shibata et al. can in fact direct reporter or *E. coli* PNP gene expression specifically to melanoma cells, as shown in U.S. Pat. No. 6,017,896, FIG. 3 and likewise operates with Tv-PNP or tm-PNP.

Therefore, human tyrosinase sequences are useful to direct Tv-PNP or tm-PNP expression to human melanoma cells. These same sequences are useful to direct other therapeutic gene expression in melanoma cells or melanocytes. Other tissue-specific genetic regulatory sequences and elements can be used to direct expression of a gene encoding a suitable purine analog nucleoside cleavage enzyme to specific cell types other than melanomas.

Delivery of the Tv-PNP or tm-PNP Gene

The construction of suitable recombinant viruses and the use of adenovirus for the transfer of Tv-PNP or tm-PNP into mammalian cells are provided. Non-viral gene delivery can also be used. Examples include diffusion of DNA in the absence of any carriers or stabilizers ("naked DNA"), DNA in the presence of pharmacologic stabilizers or carriers ("formulated DNA"), DNA complexed to proteins that facilitate entry into the cell ("molecular conjugates"), or DNA complexed to lipids. The use of lipid-mediated delivery of the bacterial PNP gene to mammalian cells is exemplified herein. More particularly, cationic liposome-mediated transfer of a plasmid containing a non-human PNP gene is demonstrated.

Other gene transfer methods are also generally applicable because the particular method for transferring the Tv-PNP gene to a cell is not solely determinative of successful target cell inhibition. Thus, gene transduction utilizing a virus-derived transfer vector, further described below, can also be used. Such methods are well known and readily adaptable for use in the gene-mediated toxin therapies described herein.

The method of delivery of the Tv-PNP or tm-PNP gene depends on its form, and a suitable method will be apparent to one skilled in the art. Such methods illustratively include administration by injection, biolistic transformation, and lipofection. The use of lipid-mediated delivery of the PNP gene to mammalian cells is exemplified herein. More particularly, cationic liposome-mediated transfer of a plasmid containing a non-human PNP gene is demonstrated. However, other gene transfer methods will also be applicable because the particular method for transferring the PNP gene to a cell is not solely determinative of successful tumor cell impairment. Thus, gene transduction, utilizing a virus-derived transfer vector, further described below, can also be used. Such methods are well known and readily adaptable for use in the gene-mediated toxin therapies described herein. Further, these methods can be used to target certain diseases and cell populations by using the targeting characteristics of a particular carrier of the gene encoding a suitable purine analog nucleoside cleavage enzyme such as Tv-PNP or tm-PNP.

Apathogenic anaerobic bacteria have been used to selectively deliver foreign genes into tumor cells. For example, *Clostridium acetobutylicum* spores injected intravenously into mice bearing tumors germinated only in the necrotic areas of tumors that had low oxygen tension. Using the assay for PNP activity described below, *Clostridium perfringens* was found to exhibit enzyme activity capable of converting MeP-dR to MeP. This finding suggests a mechanism to selectively express PNP activity in tumor masses with necrotic, anaerobic centers. Thus, tumors can be infected with strains of *Clostridium* expressing Tv-PNP or tm-PNP and then exposed to an appropriate substrate, such as fludarabine. The PNP activity of the *clostridium* bacteria growing in the anaerobic center of the tumor tissue then converts the substrate to a toxic purine analog, which then is released locally to impair the tumor cells. Additionally, other bacteria including *E. coli* and *Salmonella* can optionally be used to deliver a Tv-PNP or tm-PNP gene into tumors.

Other delivery systems operable in the present invention illustratively include vehicles such as "stealth" and other antibody-conjugated liposomes (including lipid-mediated drug targeting to colonic carcinoma), receptor-mediated targeting of DNA through cell specific ligands, lymphocyte-directed tumor targeting, and highly specific therapeutic retroviral targeting of murine glioma cells in vivo. (S. K. Huang et al., *Cancer Research*, 52:6774-6781 (1992); R. J. Debs et al., *Am. Rev. Respir. Dis.*, 135:731-737 (1987); K. Maruyama et al., *Proc. Natl. Acad. Sci. USA*, 87:5744-5748 (1990); P. Pinnaduwage and L. Huang, *Biochemistry*, 31:2850-2855 (1992); A. Gabizon and Papahadjopoulas, *Proc. Natl. Acad. Sci. USA*, 85:6949-6953 (1988); S. Rosenberg et al., *New England J. Med.*, 323:570-578 (1990); K. Culver et al., *Proc. Natl. Acad. Sci. USA*, 88:3155-3159 (1991); G. Y. Wu and C. H. Wu, *J. Biol. Chem.*, 263, No. 29:14621-14624 (1988); Wagner et al., *Proc. Natl. Acad. Sci. USA*, 87:3410-3414 (1990); Curiel et al., *Human Gene Ther.*, 3:147-154 (1992); Litzinger, *Biochimica et Biophysica Acta*, 1104:179-187 (1992); Trubetskoy et al., *Biochimica et Biophysica Acta*, 1131:311-313 (1992)). The present approach, within the context of a gene targeting mechanism either directed toward dividing tumor cells or tumor neovascularization, offers an improved methodology by which a small subset of tumor cells can be established within a growing tumor mass, which would mediate rapid tumor involution and necrosis after the appropriate signal, such as after administration of the substrate prodrug for a *T. vaginalis* purine analog nucleoside cleavage enzyme or tm-PNP present in, or proximal to, the target cells.

Methods of Treatment

The method of treatment illustratively includes transfecting or otherwise administering an inventive Tv-PNP or tm-PNP gene to cells along with exposing the cells with the Tv-PNP or tm-PNP gene or protein to an appropriate substrate. The substrate is converted to a toxic purine analog that inhibits or kills the cells expressing the Tv-PNP or tm-PNP gene as well as those bystander cells in the vicinity of the Tv-PNP or tm-PNP gene expressing cells, depending on cytotoxic purine analog concentration. The Tv-PNP or tm-PNP gene is illustratively administered directly to the targeted cells or systemically in combination with a targeting composition, such as through the selection of a particular viral vector or delivery formulation. Cells are preferably treated in vivo, within the patient to be treated, or treated in vitro, then injected into the patient. Following introduction of the Tv-PNP or tm-PNP gene into cells in the patient, the prodrug is administered, systemically or locally, in an effective amount to be converted by the Tv-PNP or tm-PNP into a cytotoxic purine analog relative to targeted cells. It is appreciated that the prodrug is optionally delivered prior to, along with, or subsequent to the administration of the inventive Tv-PNP or tm-PNP. Preferably, the prodrug is administered subsequent to administration of the Tv-PNP or tm-PNP.

Owing to difficulties in transfecting large numbers of target cells or administering Tv-PNP or tm-PNP enzyme, the cleavage kinetics of this enzyme relative to other PNPs provides surprisingly beneficial therapeutic results with substrates of clinical importance such as F-araA.

Treatment of Tumors

The Tv-PNP or tm-PNP gene is optionally used as part of a strategy to treat metastatic solid tumors, such as melanoma, pancreatic, liver or colonic carcinoma. In this method, plasmid DNA containing a Tv-PNP or tm-PNP gene under the control of tumor specific promoters is optionally used. For example, the tyrosinase promoter is highly specific for mediating expression in melanoma cells and does not lead to gene expression in most tissue types. The Tv-PNP or tm-PNP gene under regulatory control of this promoter is activated predominantly within a melanoma tumor and not elsewhere within a patient as evidenced for *E. coli* PNP in U.S. Pat. No. 6,017,896. Promoters specific for other tumor types, for example, promoters active in the rapidly dividing endothelial cells present in all solid tumors are used to specifically activate Tv-PNP or tm-PNP only within a primary or metastatic tumor. In this process, plasmid DNA containing Tv-PNP or tm-PNP under the control of a tumor specific promoter is delivered to cells using cationic liposomes. For example, based on animal studies, 100-400 mg plasmid DNA complexed to 1200-3600 micromoles of a 1:1 mixture of the lipids DOTMA (1,2-dioleyloxypropyhl-3-trimethyl ammonium bromide) and DOPE (dioleoyl phosphatidylethanolamine) could be used to deliver the Tv-PNP or tm-PNP gene to tumor metastases in patients. A prodrug in the above described amounts can then be administered. The medical treatment of tumors can be performed for financial and therapeutic benefit.

The Tv-PNP gene is optionally used to activate prodrugs for treatment of human brain cancer. In this process, a cell line producing retroviral particles containing the Tv-PNP or tm-PNP gene is injected into a central nervous system (CNS)

tumor within a patient. An MRI scanner is operable to appropriately inject the retroviral producer cell line within the tumor mass. Because the retrovirus is fully active only within dividing cells and most of the dividing cells within the cranium of a cancer patient are within the tumor, the retrovirus is primarily active in the tumor itself, rather than in non-malignant cells within the brain. Clinical features of the patient including tumor size and localization determine the amount of producer cells to be injected. For example, a volume of producer cells in the range of 30 injections of 100 microliters each (total volume 3 ml with approximately $1 \times 10^8$ producer cells/ml injected) are given under stereotactic guidance for surgically inaccessible tumors. For tumors that can be approached intraoperatively, 100 µl aliquots are injected (at about $1 \times 10^8$ cells/ml) with total injected volumes up to 10 ml using Tv-PNP or tm-PNP gene transfer, followed by F-araAMP (a prodrug of F-araA) administration. This strategy is designed to permit both bystander killing and toxicity to non-dividing cells and is designed for much greater tumor involution than previous attempts using HSV dThd kinase and ganciclovir.

Destruction of selected populations of cells is achieved by targeting the delivery of the Tv-PNP or tm-PNP gene. The natural tropism or physiology of viral vectors is exploited in targeting specific cell types. For example, retroviruses demonstrate increased activity in replicating cells. Selective retroviral-mediated gene transfer to replicating cancer cells growing within a site where the normal (nonmalignant) cells are not replicating is a therapeutically powerful targeting method in both animal and human clinical studies. Alternatively, the viral vector is directly administered to a specific site such as a solid tumor thereby concentrating gene transfer to the tumor cells as opposed to surrounding tissues. This concept of selective delivery has been demonstrated in the delivery of genes to tumors in mice by adenovirus vectors. Molecular conjugates can be developed so that the receptor binding ligand will bind only to selective cell types, as has been demonstrated for the lectin-mediated targeting of lung cancer.

Targeting a gene encoding a Tv-PNP or tm-PNP or expression of the gene to a small fraction of the cells in a tumor mass followed by substrate administration is adequate to mediate involution of tumor stasis or reduction.

Treatment of Virally Infected Cells

In addition to inhibiting, and often killing tumor cells, the processes described herein can also be used to kill virally infected cells. In a virus-killing embodiment, the selected gene transfer method is chosen for its ability to target the expression of the cleavage enzyme in virally infected cells. For example, virally infected cells utilize special viral gene sequences to regulate and permit gene expression such as virus specific promoters. Such sequences are not present in uninfected cells. The Tv-PNP or tm-PNP gene is oriented appropriately with regard to such a viral promoter to generate selective expression of the cleavage enzyme within virally infected cells. The virally infected cells thereby are susceptible to the administration of F-araA or other substrates designed to be converted to toxic form.

Administration of Genetically Engineered Cells

Also provided is a host cell transformed with a vector of the present invention.

For certain applications, cells that receive the Tv-PNP or tm-PNP gene are selected and administered to a patient. This method most commonly involves ex vivo transfer of the gene encoding the Tv-PNP or tm-PNP cleavage enzyme. The cells that receive the inventive genes are administered into the host patient where they produce the therapeutic protein until the prodrug, such as F-araA, is administered to eliminate the engineered cells. This method is useful in cell therapies such as those used on non-replicating myoblasts engineered for the production of tyrosine hydroxylase within the brain (Jiao et al., *Nature,* 362:450 (1993)).

Direct Delivery of the PNP Enzyme to Cells

Tv-PNP or tm-PNP protein with or without a prodrug is optionally delivered directly to target cells rather than the Tv-PNP or tm-PNP gene. Illustratively, a Tv-PNP or tm-PNP enzyme capable of cleaving purine analog nucleosides is manufactured by available recombinant protein techniques using a commercially available kit. As one example of a method for producing the bacterial Tv-PNP protein, the Tv-PNP coding sequence is ligated into the multiple cloning site of pGEX-4T-1 (Pharmacia, Piscataway, N.J.) so as to be "in frame" with the glutathione-s-transferase (GST) fusion protein using standard techniques (note that the cloning site of this vector allows insertion of coding sequences in all three possible translational reading frames to facilitate this step). The resulting plasmid contains the GST-PNP fusion coding sequence under transcriptional control of the IPTG-inducible prokaryotic tac promoter. *T. vaginalis* cells are transformed with the recombinant plasmid and the tac promoter induced with IPTG. IPTG-induced cells are lysed, and the GST-PNP fusion protein purified by affinity chromatography on a glutathione Sepharose 4B column. The GST-PNP fusion protein is eluted, and the GST portion of the molecule is removed by thrombin cleavage. All of these techniques and reagents are commercially available (Pharmacia, Piscataway, N.J.). Other methods for recombinant protein production are described in detail in published laboratory manuals.

Since the Tv-PNP or tm-PNP activates prodrugs into diffusible toxins, delivery the PNP protein to the exterior of the target cells prior to prodrug administration is operative to induce a therapeutic effect. The Tv-PNP or tm-PNP protein is deliverable to target cells by a wide variety of techniques. One example is the direct application of the protein with or without a carrier to a target tissue such as by directly injecting a tumor mass within an accessible site. Another example is the attachment of the Tv-PNP or tm-PNP protein to a monoclonal antibody that recognizes an antigen at the tumor site. (Villa et al., "A high-affinity human monoclonal antibody specific to the alternatively spliced EDA domain of fibronectin efficiently targets tumor neo-vasculature in vivo." *Int. J. Cancer.* 2008 Jun. 1; 122(11):2405-13. Nissim et al., "Historical development of monoclonal antibody therapeutics." *Handbook of Exp. Pharmacol.* 2008; (181):3-18.)

Methods for attaching functional proteins to monoclonal antibodies have been previously described. The Tv-PNP or tm-PNP conjugated monoclonal antibody is systemically administered, for example intravenously (IV), and attaches specifically to the target tissue. Subsequent systemic administration of the prodrug will result in the local production of diffusible toxin in the vicinity of the tumor site. A number of studies demonstrated the use of this technology to target specific proteins to tumor tissue. Other ligands, in addition to monoclonal antibodies, can be selected for their specificity for a target cell and tested according to the methods taught herein.

Protein delivery to specific targets is optionally achieved using liposomes. Methods for producing liposomes are described (e.g., *Liposomes: A Practical Approach*). Liposomes can be targeted to specific sites by the inclusion of specific ligands or antibodies in their exterior surface. An illustrative example is specific liver cell populations targeted by the inclusion of asialofetuin in the liposomal surface (Van Berkel et al., *Targeted Diagnosis and Therapy,* 5:225-249

(1991)). Specific liposomal formulations can also achieve targeted delivery as best exemplified by the so-called Stealth liposomes that preferentially deliver drugs to implanted tumors (Allen, *Liposomes in the Therapy of Infectious Diseases and Cancer,* 405-415 (1989)). After the liposomes have been injected or implanted, unbound liposome is cleared from the blood, and the patient is treated with the purine analog prodrug, such as F-araA, which is cleaved by the Tv-PNP at the targeted site. Again, this procedure requires only the availability of an appropriate targeting vehicle. In a broader sense, the strategy of targeting can be extended to specific delivery of the prodrug following either PNP protein, or gene delivery.

Alternatively, a compound is a biologically active polypeptide fragment of Tv-PNP protein which is administered to a subject. A biologically active peptide or peptide fragment optionally is a mutant form of Tv-PNP. It is appreciated that mutation of the conserved amino acid at any particular site is preferably mutatated to glycine or alanine. It is further appreciated that mutation to any neutrally charged, charged, hydrophobic, hydrophilic, synthetic, non-natural, non-human, or other amino acid is similarly operable. A still more preferred mutant involves a frame shift mutation to remove the terminal stop codon TAA and instead express a tailed mutant Tv-PNP (tmTv-PNP).

Modifications and changes are optionally made in the structure (primary, secondary, or tertiary) of the wild-type Tv-PNP protein which are encompassed within the inventive compound that may or may not result in a molecule having similar characteristics to the exemplary polypeptides disclosed herein. It is appreciated that changes in conserved amino acid residues are most likely to impact the activity of the resultant protein. However, it is further appreciated that changes in amino acids operable for ligand interaction, resistance or promotion of protein degradation, intracellular or extracellular trafficking, secretion, protein-protein interaction, post-translational modification such as glycosylation, phosphorylation, sulfation, and the like, may result in increased or decreased activity of an inventive compound while retaining some ability to alter or maintain a physiological activity. Certain amino acid substitutions for other amino acids in a sequence are known to occur without appreciable loss of activity.

In making such changes, the hydropathic index of amino acids are considered. According to the present invention, certain amino acids can be substituted for other amino acids having a similar hydropathic index and still result in a polypeptide with similar biological activity. Each amino acid is assigned a hydropathic index on the basis of its hydrophobicity and charge characteristics. Those indices are: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

Without intending to be limited to a particular theory, it is believed that the relative hydropathic character of the amino acid determines the secondary structure of the resultant polypeptide, which in turn defines the interaction of the polypeptide with other molecules. It is known in the art that an amino acid can be substituted by another amino acid having a similar hydropathic index and still obtain a functionally equivalent polypeptide. In such changes, the substitution of amino acids whose hydropathic indices are within ±2 is preferred, those within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include (original residue: exemplary substitution): (Ala: Gly, Ser), (Arg: Lys), (Asn: Gln, His), (Asp: Glu, Cys, Ser), (Gln: Asn), (Glu: Asp), (Gly: Ala), (His: Asn, Gln), (Ile: Leu, Val), (Leu: Be, Val), (Lys: Arg), (Met: Leu, Tyr), (Ser: Thr), (Thr: Ser), (Tip: Tyr), (Tyr: Trp, Phe), and (Val: Ile, Leu). Embodiments of this disclosure thus contemplate functional or biological equivalents of a polypeptide as set forth above. In particular, embodiments of the polypeptides can include variants having about 50%, 60%, 70%, 80%, 90%, and 95% sequence identity to the polypeptide of interest.

It is further appreciated that any nucleic acid substitution in the gene encoding Tv-PNP or a fragment thereof operable to produce any of the above described amino acid substitutions or to act as a silent mutation such as to produce a synonymous codon are similarly operable herein. Such substitutions and methods for their production are readily recognized by those of skill in the art.

A tm-PNP has been surprisingly found to have greater cleavage activity relative to the corresponding wild-type PNP for a given organism. A tm-PNP according to the present invention preferably involves a frame shift mutation within the terminal 150 nucleic acid bases associated with the PNP nucleotide sequence such that a termination codon common to all known PNP wild-type sequences is suppressed through a frame shift and a terminal tail added to the expressed tm-PNP amino acid sequence, the tail having between 10 and 50 additional amino acid residues. It is appreciated that the frame shift in the wild-type PNP nucleotide sequence is readily produced through insertion or deletion of one or more nucleotide bases with the proviso that the nucleotide base insertions or deletions are not a multiple of 3 upstream from the termination codon. The resultant tail corresponds to amino acid coding from adjacent PNP nucleotide sequence region relative to the wild-type nucleotide sequence stop codon or is added. The hydropathic index value of the tail of a tm-PNP and the tail length between 10 and 50 amino acid residues in length appear to be important factors in the preferential cleavage such tm-PNP enzymes exert over the clinically important prodrug substrate of F-araA relative to MeP-dR. Without intending to be bound to a particular theory, it is believed that the tail of an inventive tm-PNP modifies access of ligand to the tm-PNP prodrug binding site relative to the wild-type enzyme.

Administration of Substrates

The formula of Freidenreich et al., *Cancer Chemother. Rep.,* 50:219-244, (1966) is optionally used to determine the maximum tolerated dose of substrate for a human subject. For example, mice systemically administered 25 mg (MeP-dR) per kg per day for 9 days (9 doses total) resulted in some toxicity but no lethality. From this result a human dosage of 75 mg MeP-dR/$m^2$ was determined according to the formula: 25 mg/kg×3=75 mg/$m^2$. This amount or slightly less is expected to maximize tumor cell killing in humans without killing the subject thereby generating a favorable efficacy to safety profile. This standard of effectiveness is accepted in the field of cancer therapy. More preferably, a drug levels administered range from about 10% to 1% of the maximum tolerated dosage (for example, 7.5 mg/$m^2$-0.75 mg/$m^2$). It is understood that modes of administration that permit the substrate to remain localized at or near the site of the tumor will be effective at lower doses than systemically administered substrates.

The substrate may be administered orally, parenterally (for example, intravenously), by intramuscular injection, by intratumoral injection, by intraperitoneal injection, or transdermally. The exact amount of substrate required will vary from subject to subject, depending on age, weight, general condition of the subject, the severity of the disease that is being treated, the location and size of the tumor, the particular compound used, its mode of administration, and the like. An appropriate amount may be determined by one of ordinary skill in the art using only routine experimentation given the teachings herein. Generally, dosage will preferably be in the range of about 0.5-50 mg/m$^2$, when considering MeP-dR for example, or a functional equivalent. For a prodrug such a fludarbine, the dosage will typically be at, or below doses already known to be safe in the subject.

Depending on the intended mode of administration, the substrate can be administered in pharmaceutical compositions in the form of solid, semi-solid or liquid dosage forms, such as, for example, tablets, suppositories, pills, capsules, powders, liquids, or suspensions, preferably in unit dosage form suitable for single administration of a precise dosage. The compositions will include an effective amount of the selected substrate in combination with a pharmaceutically acceptable carrier and, in addition, may include other medicinal agents, pharmaceutical agents, carriers, or diluents. The term "pharmaceutically acceptable" as used herein refers to a material that is not biologically or otherwise undesirable, which can be administered to an individual along with the selected substrate without causing significant undesirable biological effects or interacting in a deleterious manner with any of the other components of the pharmaceutical composition in which it is contained.

For solid compositions, conventional nontoxic solid carriers include, for example, pharmaceutical grades of mannitol, lactose, starch, magnesium stearate, sodium saccharine, talc, cellulose, glucose, sucrose and magnesium carbonate. Liquid pharmaceutically administrable compositions can, for example, be prepared by dissolving or dispersing an active compound with optimal pharmaceutical adjuvants in an excipient, such as water, saline, aqueous dextrose, glycerol, ethanol, and the like to thereby form a solution or suspension. If desired, the pharmaceutical composition to be administered may also contain minor amounts of nontoxic auxiliary substances such as wetting or emulsifying agents, pH buffering agents, for example, sodium acetate or triethanolamine oleate. Actual methods of preparing such dosage forms are known, or will be apparent, to those skilled in this art; for example, see *Remington's Pharmaceutical Sciences*.

For oral administration, fine powders or granules may contain diluting, dispersing, and/or surface active agents, and may be presented in water or in a syrup, in capsules or sachets in the dry state or in a non-aqueous solution or suspension wherein suspending agents may be included, in tablets wherein binders and lubricants may be included, or in a suspension in water or a syrup. Where desirable or necessary, flavoring, preserving, suspending, thickening, or emulsifying agents may be included. Tablets and granules are preferred oral administration forms, and these may be coated.

Parenteral administration is generally by injection. Injectables can be prepared in conventional forms, either liquid solutions or suspensions, solid forms suitable for solution or prior to injection, or as suspension in liquid prior to injection or as emulsions.

Vectors Containing Tv-PNP Encoding Nucleic Acids

The present invention provides a vector containing a DNA sequence encoding a Tv-PNP. The vector may further contain a regulatory element operably linked to the nucleotide sequence such that the nucleotide sequence is transcribed and translated in a host. Preferably, the vector is a virus or a plasmid. Illustrative examples of suitable viral vectors include a retrovirus, an adenovirus, an adeno-associated virus, a vaccinia virus, a herpes virus and a chimeric viral construction such as an adeno-retroviral vector. Among useful adenovirus vectors are human adenoviruses such as type 2 or 5 and adenoviruses of animal origin illustratively including those of avian, bovine, canine, murine, ovine, porcine or simian origin.

The use of vectors derived from adeno-associated virus for the transfer of genes in vitro and in vivo has been extensively described, for example in U.S. Pat. No. 4,797,368 and U.S. Pat. No. 5,139,941. In general, the rep and/or cap genes are deleted and replaced by the gene to be transferred. Recombinant viral particles are prepared by cotransfection of two plasmids into a cell line infected with a human helper virus. The plasmids transfected include a first plasmid containing a nucleic acid sequence encoding a PNP of the present invention which is flanked by two inverted repeat regions of the virus, and a second plasmid carrying the encapsidation genes (rep and cap) of the virus. The recombinant viral particles are then purified by standard techniques.

PNP Expression

The Tv-PNP enzymes of the present invention are transcribed and translated in vivo and in vitro. In order to produce the proteins in vivo, a vector containing nucleic acids encoding a specific Tv-PNP is introduced into cells, in vivo or ex vivo. This may include reintroduction of cells back into the animal, via a vector as outlined herein. In another embodiment, the protein of interest is produced in vitro, either in a cell or in a cell-free system. Protein produced in this manner is used in vitro or introduced into a cell or animal to produce a desired result.

Expression of a Tv-PNP in mammalian cells may require a eukaryotic transcriptional regulatory sequence linked to the Tv-PNP-encoding sequences. The Tv-PNP gene can be expressed under the control of strong constitutive promoter/enhancer elements that are contained within commercial plasmids (for example, the SV40 early promoter/enhancer (pSVK30 Pharmacia, Piscataway, N.J.), Moloney murine sarcoma virus long terminal repeat (pBPV, Pharmacia), mouse mammary tumor virus long terminal repeat (pMSG, Pharmacia), and the cytomegalovirus early promoter/enhancer (pCMVβ, Clontech, Palo Alto, Calif.).

Other tissue-specific genetic regulatory sequences and elements can be used to direct expression of a gene encoding a suitable purine analog nucleoside cleavage enzyme to specific cell types other than melanomas, for example, tissue-specific promoters illustratively including a promoter of albumin, intestinal fatty acid binding protein, milk whey, neurofilament, pyruvate kinase, smooth muscle alpha-actin and villin.

The following non-limiting examples illustrate specific reaction schemes and specific inventive compounds and intermediates according to the present invention. Methods involving conventional biological techniques are described herein. Such techniques are generally known in the art and are described in detail in methodology treatises such as *Molecular Cloning: A Laboratory Manual*, 2nd ed., vol. 1-3, ed. Sambrook et al., Cold Spring Harbor Laboratory Press, Cold Spring Harbor, N.Y., 1989; and *Current Protocols in Molecular Biology*, ed. Ausubel et al., Greene Publishing and Wiley- Interscience, New York, 1992 (with periodic updates). Immunological methods (e.g., preparation of antigen-specific antibodies, immunoprecipitation, and immunoblotting) are described, e.g., in *Current Protocols in Immunology*, ed. Coligan et al., John Wiley & Sons, New York, 1991; and *Methods of Immunological Analysis*, ed. Masseyeff et al., John Wiley & Sons, New York, 1992.

Various aspects of the present invention are illustrated by the following non-limiting examples. The examples are for illustrative purposes and are not a limitation on any practice of the present invention. It will be understood that variations and modifications can be made without departing from the spirit and scope of the invention. While the examples are generally directed to mammalian cells, tissue, fluids, or subjects, a person having ordinary skill in the art recognizes that similar techniques and other techniques known in the art readily translate the examples to other mammals such as humans. Reagents illustrated herein are commonly cross reactive between mammalian species or alternative reagents with similar properties are commercially available, and a person of ordinary skill in the art readily understands where such reagents may be obtained.

Substrate Selection

Suitable substrates are characterized by being relatively nontoxic to a mammalian cell compared to the cytotoxic cleaved purine base analog. Below are listed some illustrative examples of substrates. Common abbreviation(s) are included after some of the compounds and offset by a semicolon:

9-(β-D-arabinofuranosyl)-2-fluoroadenine; F-araA, fludarabine 9-(2-deoxy-β-D-ribofuranosyl]-6-methylpurine; MeP-dR 9-(β-D-ribofuranosyl)-2-amino-6-chloro-1-deazapurine; ACDP-R 7-(β-D-ribofuranosyl)-3-deazaguanine 2-fluoro-2'-deoxyadenosine; F-dAdo 9-(5-deoxy-β-D-ribofuranosyl)-6-methylpurine 2-fluoro-5'-deoxyadenosine 2-chloro-2'-deoxyadenosine; Cl-dAdo, Cladribine 5'-amino-5'-deoxy-2-fluoroadenosine 9-(5-amino-5-deoxy-β-D-ribofuranosyl)-6-methylpurine 9-(α-D-ribofuranosyl)-2-fluoroadenine 9-(2,3-dideoxy-β-D-ribofuranosyl)-6-methylpurine 2',3'-dideoxy-2-fluoroadenosine 9-(3-deoxy-β-D-ribofuranosyl]-6-methylpurine 2-fluoro-3'-deoxyadenosine 9-(α-L-lyxofuranosyl)-2-fluoroadenine 9-(α-L-lyxofuranosyl)-6-methylpurine 9-(6-deoxy-β-D-allofuranosyl)-6-methylpurine 9-(6-deoxy-β-D-allofuranosyl)-2-fluoroadenine 9-(6-deoxy-α-L-talofuranosyl)-6-methylpurine 9-(6-deoxy-α-L-talofuranosyl)-2-fluoroadenine 9-(2,6-dideoxy-β-D-allofuranosyl)-6-methylpurine 9-(2,6-dideoxy-β-D-allofuranosyl)-2-fluoroadenine 9-(2,6-dideoxy-α-L-talofuranosyl)-6-methylpurine 9-(2,6-dideoxy-α-L-talofuranosyl)-2-fluoroadenine 9-(6,7-dideoxy-α-L-hept-6-ynofuranosyl)-6-methylpurine 9-(6,7-dideoxy-α-L-hept-6-ynofuranosyl)-2-fluoroadenine 9-(6,7-dideoxy-β-D-hept-6-ynofuranosyl)-6-methylpurine 9-(6,7-dideoxy-β-D-hept-6-ynofuranosyl)-2-fluoroadenine 9-(2,6,7-trideoxy-α-L-hept-6-ynofuranosyl)-6-methylpurine 9-(2,6,7-trideoxy-α-L-hept-6-ynofuranosyl)-2-fluoroadenine 9-(2,6,7-trideoxy-β-D-hept-6-ynofuranosyl)-6-methylpurine 9-(2,6,7-trideoxy-β-D-hept-6-ynofuranosyl)-2-fluoroadenine 9-(2,3-dideoxy-3-hydroxymethyl-α-D-ribofuranosyl)-6-thioguanine 9-(5,5-di-C-methyl-β-D-ribofuranosyl)-2-fluoro-adenine 9-(5,5-di-C-methyl-β-D-ribofuranosyl)-6-methylpurine 9-(5-deoxy-5-iodo-β-D-ribofuranosyl)-2-fluoroadenine 9-(5-deoxy-5-iodo-β-D-ribofuranosyl)-6-methylpurine 9-(5-deoxy-5-methylthio-β-D-ribofuranosyl)-2-fluoroadenine 9-(5-deoxy-5-methylthio-β-D-ribofuranosyl)-6-methylpurine Further examples are found in Ichikawa E. and Kato K., *Curr. Med. Chem.* 2001 March; 8(4): 385-423.

It is appreciated that some substrates would be expected to be better tolerated than others. For example, F-araA is cleaved at a faster rate by Tv-PNP as compared to other known enzymes so as to provide greater therapeutic options.

Example 1

Synthesis of Tv-PNP Expression Vectors

*T. vaginalis* genomic DNA is obtained with a first DNA clone from metronidazole-resistant strain (R: CDC955) and a second DNA clone from sensitive strain (S3: CDC520). TvPNP gene is amplified by PCR using following primers from both samples using AccuPrime Pfx supermix (Invitrogen). The primers are designed based on the TvPNP sequence downloaded from TIGR trichomonas genome project web site. The sequence is currently available at GenBank (XM_001323400). Tv-PNP primers used herein included with parenthetical restriction sites therein: forward primer TvPNP-F: 5'-GTTAACGGATCCATGGCAACACCCCAT-AACTCTGCT-3' (HpaI & BamHI) (SEQ ID NO: 1). Tv-PNP reverse primers TvPNP-R: 5'-TCTAGAGTTAACGTCCT-TATAATTTGATTGCTGCTTC-3' (XbaI & HpaI) (SEQ ID NO: 2) and TvPNP-R1: 5'-ATAGTTTAGATCCGAGGAC-CAATCAT-3' (SEQ ID NO: 3). The nucleotide sequence of wild-type Tv-PNP is illustrated as SEQ ID NO: 4. The amino acid sequence of wild-type Tv-PNP is SEQ ID NO: 5.

Figure 3:
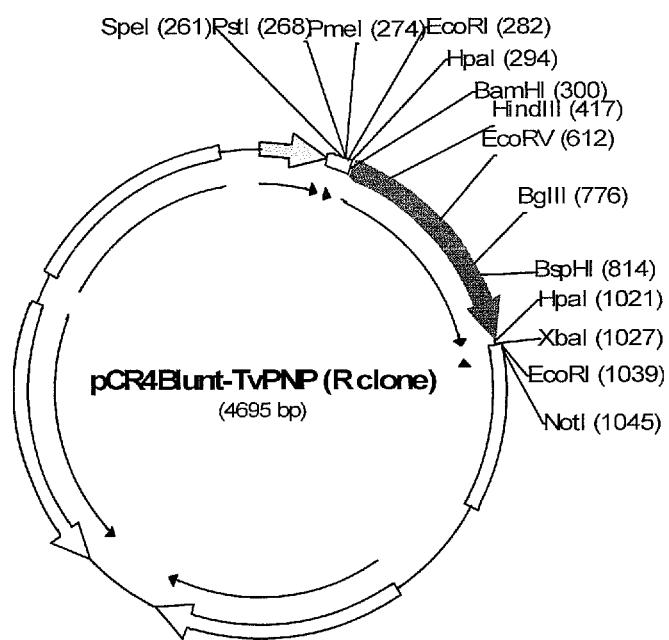
FIG. 3 is a restriction site map of an inventive vector clone denoted as pCR4blunt-TvPNP.
Figure 4:
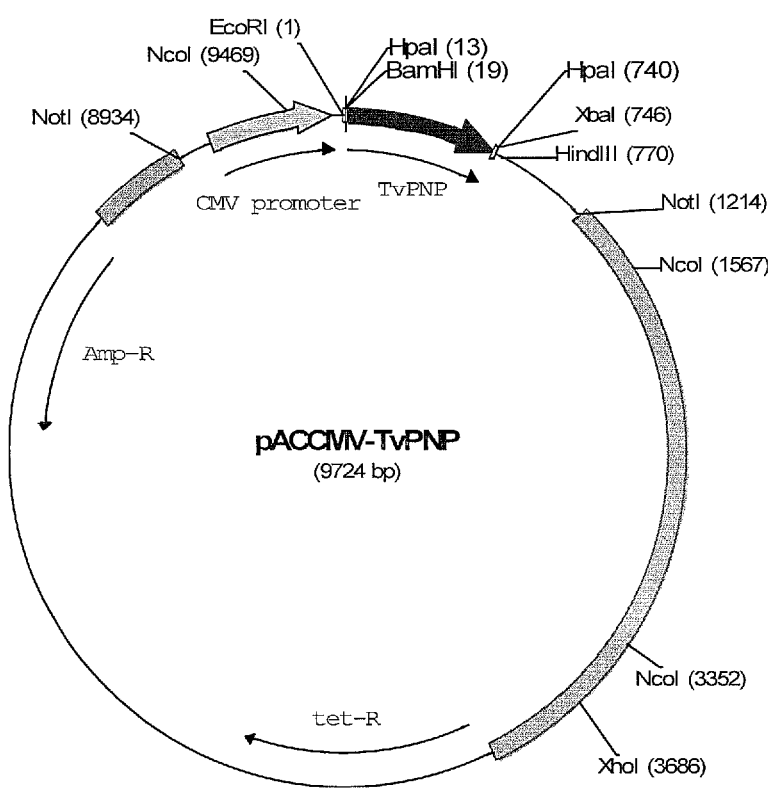
FIG. 4 is a restriction site map of an inventive adenovirus vector expressing Tv-PNP denoted as pACCMV-TvPNP and inclusive of the clone of FIG. 3.

The first round of PCR is performed using TvPNP-F and Tv-PNPR1 primers. Then nested PCR (second round) is performed using the product from the first round PCR and primers TvPNP-F and TvPNP-R. The PCR product is cloned into pCR4Blunt-Topo vector (Invitrogen) and sequenced (clone ID=pCR4 Blunt-TvPNP) as depicted in FIG. 3. S strain contains one base change from the TIGR sequence, but it does not change the codon Arg102 (CGC→CGT). Since the R clone matches the TIGR sequence, the TvPNP(R) clone is used for further cloning. To generate adenovirus expressing TvPNP, TvPNP(R) of FIG. 3 is digested with EcoRI and XbaI and cloned into EcoRI and XbaI sites of pACCMV.pLpA adenovirus transfer vector. The pACCMV-TvPNP as depicted in FIG. 4 is co-transfected with pJM17 (Microbix) to obtain recombinant Ad-TvPNP via homologous recombination in 293 cells. The resulting Ad-TvPNP is identified by Tv-PNP specific PCR and Tv-PNP activity assay.

Figure 5:
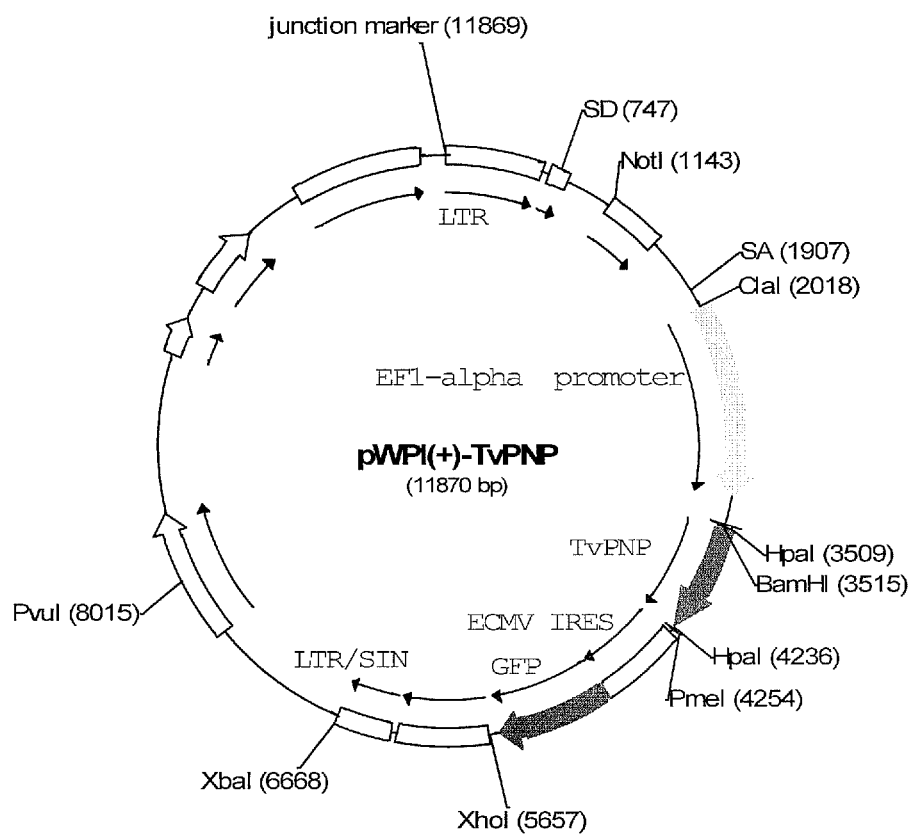
FIG. 5 is a restriction site map of an inventive vector lentivirus expressing Tv-PNP with EGFP co-expression and denoted as pWPI(+)-TvPNP and inclusive of the clone of FIG. 3.

Two different vectors are used to generate Lenti-TvPNP viruses. TvPNP(R) as depicted in FIG. 3 is cloned into a modified pWPI vector (originally from Addgene.org; that is modified to contain more restriction sites for cloning purpose (pWPI-linker(+))). pWPI vector expresses enhanced green fluorescent protein (EGFP) under internal ribosome entry site (IRES) control. TvPNP(R) is isolated from pCR4Blunt-TvPNP using PmeI and XbaI then cloned into SnaBI and SpeI sites of pWPI-linker(+) vector of FIG. 5. PmeI and SnaBI are blunt end cut and XbaI and SpeI generate the same overhangs.

Figure 6:
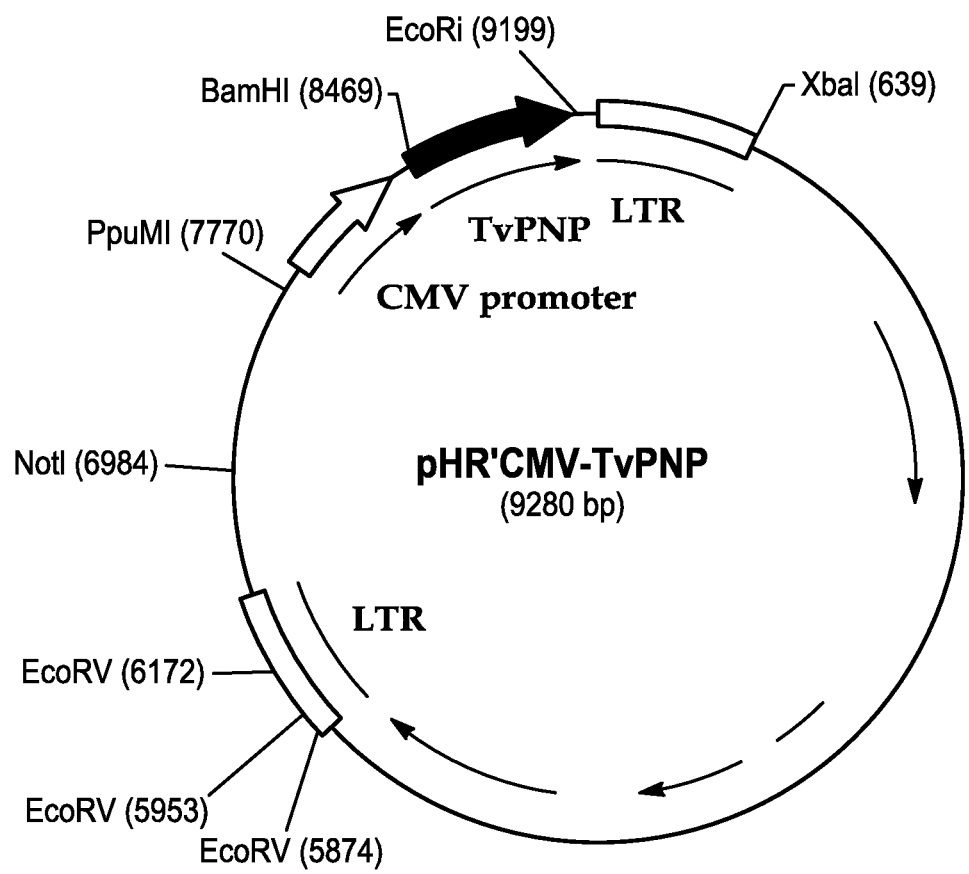
FIG. 6 is a restriction site map of an inventive vector lentivirus expressing Tv-PNP absent EGFP co-expression and denoted as pHR'CMV-TvPNP and inclusive of the clone of FIG. 3.

TvPNP(R) is separately cloned into pHR'CMV Luc W Sin-18 vector (per *J. Bio. Chem.*, Published on Oct. 1, 2004 as Manuscript M410370200) in place of luciferase gene to generate cell lines expressing TvPNP without coexpressing EGFP. TvPNP(R) is isolated from pCR4Blunt-TvPNP using BamHI and HpaI then cloned into BamHI and XhoI (blunt ended using Klenow fragment) sites of pHR'CMV Luc W Sin-18 vector depicted in FIG. 6.

Example 2

Identifying Candidate Prodrugs for Tv-PNP Enzymes

The following method is useful to identify substrates that are cleaved more efficiently by the wild-type Tv-PNP than by wild-type *E. coli* PNP or other PNPs. Prodrugs identified by this method can then be further assessed in animal studies for determination of toxicity, suitability for administration with various pharmaceutical carriers, and other pharmacological properties.

The method quantitatively measures the cleavage of substrates in vitro. The purine analog nucleosides (0.1 mM in 500 μl of 100 mM HEPES, pH 7.4, 50 mM potassium phosphate) are combined with 100 μg/ml Tv-PNP or wild-type *E. coli* PNP. The reaction mixtures are incubated at 25° C. for 1 hour, and the reactions stopped by boiling each sample for 2 minutes. Protein concentration and time of assay are varied depending on activity of enzyme for a particular substrate. Each sample is analyzed by reverse phase HPLC to measure conversion from substrate to product. The nucleoside and purine analogs are eluted from a Spherisorb ODSI (5 μm) column (Keystone Scientific, Inc., State College, Pa.) with a solvent containing 50 mM ammonium dihydrogen phosphate (95%) and acetonitrile (5%). Products are detected by absorbance at 254 nm, and are identified by comparing their retention times and absorption spectra with authentic control samples.

Table 1 shows the activity of wild-type *E. coli* PNP enzyme in comparison to wild-type Tv-PNP in the presence of various substrates. Numerous compounds are tested for efficiency as substrate for Tv-PNP in parallel comparison with *E. coli* PNP. The compounds include various analogs of adenosine, of inosine, of MeP-dR, and of fluoro- or chloro-substituted adenosine. The enzymes are incubated with 100 micromolar of each compound listed in the table and the rate of enzymatic cleavage is determined by HPLC separation of the base from the nucleoside. As shown in Table 1, Tv-PNP cleaves F-araA at a rate (32,000 nanomoles per milligrams per hour) that is approximately 23-times the rate that *E. coli* PNP cleaves F-araA (1,250 nanomoles per milligrams per hour). The result is further confirmed as shown in FIG. 1 that the catalytic efficiency of Tv-PNP with F-araA is 25-fold that of the catalytic efficiency of *E. coli* PNP with F-araA ($V_{max}/K_m$ of 944 vs. 38). It is appreciated that the greater biological activity of the Tv-PNP enzyme allows for greater activity in impairing abnormal cell growth when the Tv-PNP is used for treatment of pathological conditions using F-araA as a prodrug substrate. Since F-araA is reported to cause complete responses in tumor expressing wild-type *E. coli* PNP enzyme, an at least 23-fold increase in the generation of toxic F-Ade using the wild-type Tv-PNP and F-araA combination leads to improved anti-tumor activity.

It is also noted from Table 1 that Tv-PNP has greater activities towards 2-Cl-2'-deoxyadenosine (Cl-dAdo, cladribine) when compared to *E. coli* PNP. The Tv-PNP cleaves Cl-dAdo at a specific activity of 320,000 nanomoles per milligram per hour whereas the same Cl-dAdo is cleaved by *E. coli* at a specific activity of only 39,000 nanomoles per milligram per hour.

TABLE 1

Comparison of substrate activity of Tv-PNP and Wild-type *E. coli* PNP; a "—" represents no detected cleavage.

| Substrate | *T. vaginalis* PNP | *E. coli* PNP |
|---|---|---|
| Adenosine | 501,000 | 398,000 |
| 9-β-D-arabinofuranosyl-adenine | 38,000 | 610 |
| 9-β-D-xylofuranosyl-adenine | 2 | <2 |
| 3'-deoxyadenosine (cordycepin) | 2,000 | <2 |
| 2',3'-dideoxyadenosine | 640 | <2 |
| 5'-deoxyadenosine | 50,000 | 8,400 |
| 5'-amino-5'-deoxyadenosine | 4,200 | 540 |
| 5'-carboxamide of adenosine | 33 | <1 |
| 9-β-D-pyranosyl-adenine | 2 | <1 |
| 2'-O$^{methyl}$-adenosine | <10 | <1 |
| 9-α-L-lyxofuranosyl-adenine | 22,000 | 3,700 |
| Inosine | 154,000 | 342,000 |
| 2'-deoxyinosine | 660,000 | 733,000 |
| 9-β-D-arabinofuranosyl-hypoxanthine | 48 | 61 |
| 9-β-D-arabinofuranosyl-guanine | 16 | 310 |
| 7-β-D-ribosyl-hypoxanthine | 2,300 | 5,200 |
| 7-β-D-ribosyl-6-thioguanine | 435 | 66 |
| Guanosine | 14,000 | 156,000 |
| 9-β-D-ribofuranosyl-6-methylpurine | 155,000 | 96,000 |
| 9-[5-deoxy-β-D-ribofuranosyl]-6-methylpurine | 3,600 | 406 |
| 9-[2-deoxy-β-D-ribofuranosyl]-6-methylpurine | 484,000 | 528,000 |
| 9-[β-D-arabinofuranosyl]-6-methylpurine | 570 | 14 |
| 9-[2-deoxy-α-D-ribofuranosyl]-6-methylpurine | <8 | <1 |
| 9-[5-methyl-(talo)-β-D-ribofuranosyl]-6-methylpurine | 8,400 | 915 |
| 9-[5-methyl-(allo)-β-D-ribofuranosyl]-6-methylpurine | 223 | 47 |

TABLE 1-continued

Comparison of substrate activity of Tv-PNP and Wild-type E. coli PNP; a "—" represents no detected cleavage.

| Substrate | T. vaginalis PNP | E. coli PNP |
|---|---|---|
| 9-[5-methyl-(talo)-2-deoxy-β-D-ribofuranosyl]-6-methylpurine | 103,000 | 3,600 |
| 9-[5,5-dimethyl-β-D-ribofuranosyl]-6-methylpurine | <8 | <1 |
| 9-α-L-lyxofuranosyl-6-methylpurine | 10,000 | 320 |
| 7-[2-deoxy-α-L-lyxofuranosyl]-6-methylpurine | <8 | <1 |
| 9-[5-deoxy-α-L-lyxofuranosyl]-6-methylpurine | 246 | 20 |
| 9-[5-deoxy-5-iodo-α-L-lyxofuranosyl]-6-methylpurine | <8 | <1 |
| 2-F-2'-deoxyadenosine (F-dAdo) | 400,000 | 435,000 |
| 2-F-adenosine | 185,000 | 215,000 |
| 9-β-D-arabinofuranosyl-2-F-adenine (fludarabine) | 32,000 | 1,250 |
| 2-F-5'-deoxy-adenosine | 50,000 | 29,000 |
| 9-α-L-lyxofuranosyl-2-F-adenine | 28,200 | 7,800 |
| 2-Cl-2'-deoxyadenosine (Cl-dAdo) | 352,000 | 39,000 |
| 2-Cl-2'-deoxyadenosine (β-L) | <8 | <1 |
| 2-Cl-2'-deoxyadenosine (α-L) | <8 | <1 |

Tv-PNP and wild-type E. coli PNP are substantially similar in both structure and functionality. The instant discovery and quantification that the Tv-PNP and E. coli differ greatly in the efficiency of cleaving prodrugs to cytotoxic compounds is contradictory to the conventional understanding that Tv-PNP does not have appreciable activity towards F-araA (Wang et al., id.), indicating the novelty of this observation.

By this analysis, Tv-PNP has more activity for fludarabine, cladribine, analog of cordycepin, analog of 2',3'-dideoxyadenosine, 5'-methyl(talo)-6-methylpurine-riboside, 5'-methyl(talo)-2'-deoxy-6-methylpurine-riboside, 5'-methyl(allo)-6-methylpurine-riboside, 2-F-5'-deoxyadenosine, or 2-F-α-L-lyxo-adenine as compared to wild-type E. coli PNP. Thus, these substrates are preferred candidate prodrugs which are eligible for further assessment for use in the methods and compositions described herein to treat a pathological condition and in particular those prodrugs commercially available in USP grade.

Example 3

Comparison of the Ability of Various PNPs to Cleave MeP-dR and F-araA

The relative cleavage activity of PNPs of various origins is compared to determine the optimal enzyme for cleavage of the important chemotherapeutics MeP-dR and F-araA by the procedure of Example 2. Enzymes of various purities are incubated with 100 μM MeP-dR or F-araA and the rate of cleavage is determined by measuring the production of product (MeP or F-Ade) by HPLC as described in Example 2. The results are provided in Table 2.

TABLE 2

| Organism | MeP-dR | F-araA nmoles/mg/hr | MeP-dR/F-araA |
|---|---|---|---|
| human PNP | 35 | <1 | >35 |
| T. vaginalis PNP | 536,000 | 30,000 | 18 |
| E. coli PNP | 528,000 | 1,250 | 422 |
| A. areogenes PNP | 6,638 | 10 | 464 |
| A. Laidlawii PNP | 6,090 | 19 | 320 |
| Klebsiella sp PNP | 11,432 | 32 | 357 |
| Salmonella typhimurium PNP | 9,150 | 20 | 458 |
| B. cereus PNP | 1,400,000 | 13,000 | 108 |
| Tularemia PNP | 4,900 | 18 | 272 |
| T. Bruceii hydrolase | 750 | <1 | >750 |

TABLE 2-continued

| Organism | MeP-dR | F-araA nmoles/mg/hr | MeP-dR/F-araA |
|---|---|---|---|
| E. Coli PNP mutant M65V | 1823 | 3.9 | 469 |
| tm-PNP | 948 | 4.8 | 198 |

Example 4

30 Residue Terminal Tailed E. Coli PNP (tm-PNP) Expression and Prodrug Cleavage

A nucleotide sequence derived from wild-type E. coli PNP and noted on a sequence confirmed region of nucleotide bases was cloned into pACCMV.p1pA adenovirus transfer vector. This sequence varies from wild-type E. coli PNP in lacking an adenosine base that is otherwise present as residue 1634 (FIG. 7). This base deletion to produce "GGTAA" in wild-type E. coli PNP would have been "GAG" ($239^{th}$ codon corresponding to glutamic acid) and "TAA" corresponding to termination codon. The resultant frame shift produces a 30 amino acid tail in place of a glutamic acid as the terminal ($239^{th}$ residue) of glutamic acid found in wild-type E. coli PNP. A cogenics sequence corresponding to this tail mutant PNP is provided in FIG. 7 with the initiation (atg) and termination (taa) codons of the tail mutant PNP highlighted as well as the frame shift region of the adenovirus transfer vector sequence. Otherwise, a nucleotide sequence extending between bases 919 and 1633 of FIG. 7 corresponds to a wild-type PNP nucleotide sequence.

The amino acid sequence of the tm-PNP produced by expression of the nucleotide sequence of FIG. 7 is provided in FIG. 8. The 30 amino acid tail provided in place of the terminal glutamic acid in wild-type E. coli PNP is highlighted in FIG. 8 and is illustrated as SEQ ID NO: 8. The nucleotide sequence cloned into the adenovirus transfer vector, a portion of which is shown in SEQ ID NO: 6 includes a nucleotide sequence extending between bases 919 and 1722 (SEQ ID NO: 7) that includes a 30 amino acid tail mutant (SEQ ID NO: 8) in place of the terminal glutamic acid amino acid residue found in wild-type E. coli PNP.

The resultant tm-PNP was tested for its ability to cleave MeP-dR and F-araA as detailed in Example 3. This tm-PNP had a MeP-dR/F-araA ratio of 198. This corresponds to a wild-type E. coli PNP ratio of 422 (Table 2) and represents a 2.3-fold selectivity of cleavage of F-araA. Accordingly, tm-PNP represents a preferred enzyme for use with the prodrug F-araAMP in the treatment of solid tumors.

The tm-PNP compares favorably in cleavage ability with substitution mutants of *E. coli* PNP. A number of substitution mutation *E. coli* PNPs are detailed in WO 03/035012 and include amino acid residue valine substitution in place of methionine at position 65 (counting from the fMET) of the wild-type *E. coli* PNP protein sequence (M65V). The EcoRI and XbaI sites of pACCMV.pLpA adenovirus transfer virus ratio for M65V that lacks an inventive amino acid tail for purified enzyme was 593, while the enzyme expressed in tumors injected with an adenovirus vector encoding for the substitution mutant *E. coli* PNP was 469±52. As with all cleavage ratio results, these results are normalized based on equimolar quantities of substrate.

In vivo efficacy experiments indicate that tm-PNP shows considerably greater antitumoral activity relative to M65V with these differences attributed to differential EcoRI and XbaI sites of pACCMV.pLpA adenovirus transfer vector cleavage ratio.

Example 5

24 Residue Terminal Tailed *E. Coli* PNP (tm-PNP) Expression and Prodrug Cleavage The nucleotide sequence of FIG. 7 is modified to insert an adenosine base after base 1705 to create a termination codon (TAA) with a 24 amino acid tail added in place of glutamic acid at the terminus of wild-type *E. coli* PNP. This 24 amino acid tail added tm-PNP is a cloned sequence into pACCMV-.pLpA adenovirus transfer vector as detailed in Example 4 and is provided in SEQ ID NO: 9. The expressed amino acid sequence is provided in SEQ ID NO: 10.

Example 6 tmTv-PNP with 30 Residue Terminal Tail

The procedure of Example 4 is repeated with a TAA deletion from Tv-PNP and added a polypeptide tail in an adenovirus expression vector. This 30 amino acid tailed tmTv-PNP is a cloned sequence into pACCMV.pLpA adenovirus transfer vector as detailed in Example 4 and is provided in SEQ ID NO: 11. The expressed amino acid sequence is provided in SEQ ID NO: 12.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

---

The invention claimed is:

1. A process for inhibiting a mammalian cancerous cell or virally infected cell comprising:
   providing a tail mutant purine nucleoside phosphorylase enzyme having a tail of between 10 and 50 additional amino acid residues and corresponding to a frame shift mutation within a terminal 150 nucleic acid residues associated with a nucleotide sequence associated with a wild type purine nucleoside phosphorylase in proximity to the cancerous mammalian cell or the virally infected cell; and
   exposing the enzyme to a cleavable substrate to yield a cytotoxic purine analog.

2. The process of claim 1 wherein said substrate is 9-(β-D-arabinofuranosyl)-2-fluoroadenine (fludarabine), cladribine, an analog of cordycepin, an analog of 2',3'-dideoxyadenosine, 5'-methyl(talo)-6-methyl-purine-riboside, 5'-methyl(talo)-2'-deoxy-6-methylpurine-riboside, 5'-methyl(allo)-6-methylpurine-riboside, 2-F-5'-deoxyadenosine, or 2-F-α-L-lyxo-adenine.

3. The process of claim 1 wherein providing the enzyme is by administering a viral vector coding a nucleotide sequence for said enzyme expressible in said cell.

4. The process of claim 1 wherein providing said enzyme is by direct injection, infection, lipofection, or biolistic administration of a nucleotide sequence for the enzyme expressible in the cell.

5. The process of claim 1 wherein providing said enzyme is by direct injection of the enzyme proximal to said cell.

6. The process of claim 1 wherein providing said enzyme is by administration to a subject or a subject cell modified to express said tail mutant purine nucleoside phosphorylase.

7. The process of claim 1 wherein providing is by intracellular delivery of an expressible nucleotide sequence encoding said enzyme.

* * * * *

SEQUENCE LISTING

```
<160> NUMBER OF SEQ ID NOS: 12

<210> SEQ ID NO 1
<211> LENGTH: 36
<212> TYPE: DNA
<213> ORGANISM: Trichomonas vaginalis

<400> SEQUENCE: 1
gttaacggat ccatggcaac accccataac tctgct                         36

<210> SEQ ID NO 2
<211> LENGTH: 37
<212> TYPE: DNA
<213> ORGANISM: Trichomonas vaginalis

<400> SEQUENCE: 2
tctagagtta acgtccttat aatttgattg ctgcttc                        37

<210> SEQ ID NO 3
<211> LENGTH: 26
<212> TYPE: DNA
<213> ORGANISM: Trichomonas vaginalis

<400> SEQUENCE: 3
atagtttaga tccgaggacc aatcat                                    26

<210> SEQ ID NO 4
<211> LENGTH: 720
<212> TYPE: DNA
<213> ORGANISM: Trichomonas vaginalis
```

-continued

```
<400> SEQUENCE: 4
ctttcatggc aacaccccat aactctgctc aggttggcga tttcgctgaa acagtcctca    60
tgtgcggtga tccactccgc gctaagctca ttgctgagac atatcttgaa atccaaagc    120 ttgtcaacaa tgttcgtggc attcaaggct acaccggcac atacaaggga agccaatct    180 ctgtcatggg ccatggtatg ggcttgccat caatctgcat ctatgcagag gagctttact   240
ccacatacaa ggtcaagaca atcatccgtg ttggtacatg cggcgcaatt gacatggaca   300
tccacacacg cgatatcgtt atcttcacct ctgctggtac aaactccaag atcaacagaa   360
tccgcttcat ggatcacgat tatccagcca cagcatcttt cgatgttgtt tgcgccttag   420
ttgatgctgc taaggaactc aacatcccag ctaaggtcgg taagggattc tcaacagatc   480
tcttctacaa tccacaaacc gaactcgcac agctcatgaa caagttccac ttcctcgctg   540
ttgaaatgga atctgctggc ctcttcccaa ttgctgacct ttatggcgca agagctggct   600
gcatctgcac agtttcagat cacatcctcc accatgaaga acaacagcc gaagaacgcc    660 agaactcctt ccaaaacatg atgaagatcg cacttgaagc agcaatcaaa ttataaggac   720
```

<210> SEQ ID NO 5
<211> LENGTH: 236
<212> TYPE: PRT
<213> ORGANISM: Trichomonas vaginalis

<400> SEQUENCE: 5

```
Met Ala Thr Pro His Asn Ser Ala Gln Val Gly Asp Phe Ala Glu Thr
1               5                   10                  15

Val Leu Met Cys Gly Asp Pro Leu Arg Ala Lys Leu Ile Ala Glu Thr
            20                  25                  30

Tyr Leu Glu Asn Pro Lys Leu Val Asn Asn Val Arg Gly Ile Gln Gly
        35                  40                  45

Tyr Thr Gly Thr Tyr Lys Gly Lys Pro Ile Ser Val Met Gly His Gly
    50                  55                  60

Met Gly Leu Pro Ser Ile Cys Ile Tyr Ala Glu Glu Leu Tyr Ser Thr
65                  70                  75                  80

Tyr Lys Val Lys Thr Ile Ile Arg Val Gly Thr Cys Gly Ala Ile Asp
                85                  90                  95

Met Asp Ile His Thr Arg Asp Ile Val Ile Phe Thr Ser Ala Gly Thr
            100                 105                 110

Asn Ser Lys Ile Asn Arg Ile Arg Phe Met Asp His Asp Tyr Pro Ala
        115                 120                 125

Thr Ala Ser Phe Asp Val Val Cys Ala Leu Val Asp Ala Ala Lys Glu
    130                 135                 140

Leu Asn Ile Pro Ala Lys Val Gly Lys Gly Phe Ser Thr Asp Leu Phe
145                 150                 155                 160

Tyr Asn Pro Gln Thr Glu Leu Ala Gln Leu Met Asn Lys Phe His Phe
                165                 170                 175

Leu Ala Val Glu Met Glu Ser Ala Gly Leu Phe Pro Ile Ala Asp Leu
            180                 185                 190

Tyr Gly Ala Arg Ala Gly Cys Ile Cys Thr Val Ser Asp His Ile Leu
        195                 200                 205

His His Glu Glu Thr Thr Ala Glu Glu Arg Gln Asn Ser Phe Gln Asn
    210                 215                 220

Met Met Lys Ile Ala Leu Glu Ala Ala Ile Lys Leu
225                 230                 235
```

<210> SEQ ID NO 6
<211> LENGTH: 2134
<212> TYPE: DNA
<213> ORGANISM: Trichomonas vaginalis

<400> SEQUENCE: 6

```
tctaggcggc cgcgatctat acattgaatc aatattggca attagccata ttagtcattg      60
gttatatagc ataaatcaat attggctatt ggccattgca tacgttgtat ctatatcata     120
atatgtacat ttatattggc tcatgtccaa tatgaccgcc atgttgacat tgattattga     180
ctagttatta atagtaatca attacggggt cattagttca tagcccatat atggagttcc     240
gcgttacata acttacggta aatggcccgc ctggctgacc gcccaacgac ccccgcccat     300
tgacgtcaat aatgacgtat gttcccatag taacgccaat agggactttc cattgacgtc     360
aatgggtgga gtatttacgg taaactgccc acttggcagt acatcaagtg tatcatatgc     420
caagtccgcc ccctattgac gtcaatgacg gtaaatggcc cgcctggcat tatgcccagt     480
acatgacctt acgggacttt cctacttggc agtacatcta cgtattagtc atcgctatta     540
ccatggtgat gcggttttgg cagtacacca atgggcgtgg atagcggttt gactcacggg     600
gatttccaag tctccacccc attgacgtca atgggagttt gttttggcac caaaatcaac     660
gggactttcc aaaatgtcgt aataacccccg cccgttgac gcaaatgggc ggtaggcgtg     720
tacggtggga ggtctatata agcagagctc gtttagtgaa ccgtcagatc cggtcgcgcg     780
aattcgagct cggtacccgg ggatccggtg gtggtgcaaa tcaaagaact gctcctcagt     840
ggatgttgcc tttacttcta ggcctgtacg gaagtgttac ttctgctcta aaagctgcgg     900
aattgtaccc gcggccgcat ggctacccca cacattaatg cagaaatggg cgatttcgct     960
gacgtagttt tgatgccagg cgacccgctg cgtgcgaagt atattgctga aactttcctt    1020
gaagatgccc gtgaagtgaa caacgttcgc ggtatgctgg gcttcaccgg tacttacaaa    1080
ggccgcaaaa tttccgtaat gggtcacggt atgggtatcc cgtcctgctc catctacacc    1140
aaagaactga tcaccgattt cggcgtgaag aaaattatcc gcgtgggttc ctgtggcgca    1200
gttctgccgc acgtaaaact gcgcgacgtc gttatcggta tgggtgcctg caccgattcc    1260
aaagttaacc gcatccgttt taaagaccat gactttgccg ctatcgctga cttcgacatg    1320
gtgcgtaacg cagtagatgc agctaaagca ctgggtattg atgctcgcgt gggtaacctg    1380
ttctccgctg acctgttcta ctctccggac ggcgaaatgt cgacgtgat ggaaaaatac    1440
ggcattctcg gcgtggaaat ggaagcggct ggtatctacg gcgtcgctgc agaatttggc    1500
gcgaaagccc tgaccatctg caccgtatct gaccacatcc gcactcacga gcagaccact    1560
gccgctgagc gtcagactac cttcaacgac atgatcaaaa tcgcactgga atccgttctg    1620
ctgggcgata aggtaagcg gccgcgggga tcctctagag tcgacctgca ggcatgcaag    1680
cttgggatct ttgtgaagga accttacttc tgtggtgtga cataattgga caaactacct    1740
acagagattt aaagctctaa ggtaaatata aaatttttaa gtgtataatg tgttaaacta    1800
ctgattctaa ttgtttgtgt attttagatt cacagtccca aggctcattt caggcccctc    1860
agtcctcaca gtctgttcat gatcataatc agccatacca catttgtaga ggttttactt    1920
gctttaaaaa acctcccaca cctcccccctg aacctgaaac ataaaatgaa tgcaattgtt    1980
gttgttaact tgtttattgc agcttataat ggttacaaat aaagcaatag catcacaaat    2040
ttcacaaata aagcattttt ttcactgcat tctagttgtg gtttgtccaa actcatcaat    2100
gtatcttatc atgtctggat cgcggccgcc taga                                2134
```

-continued

```
<210> SEQ ID NO 7
<211> LENGTH: 804
<212> TYPE: DNA
<213> ORGANISM: Trichomonas vaginalis

<400> SEQUENCE: 7
atggctaccc cacacattaa tgcagaaatg ggcgatttcg ctgacgtagt tttgatgcca      60
ggcgacccgc tgcgtgcgaa gtatattgct gaaactttcc ttgaagatgc ccgtgaagtg     120
aacaacgttc gcggtatgct gggcttcacc ggtacttaca aaggccgcaa aatttccgta     180
atgggtcacg gtatgggtat cccgtcctgc tccatctaca ccaaagaact gatcaccgat     240
ttcggcgtga agaaaattat ccgcgtgggt tcctgtggcg cagttctgcc gcacgtaaaa     300
ctgcgcgacg tcgttatcgg tatgggtgcc tgcaccgatt ccaaagttaa ccgcatccgt     360
tttaaagacc atgactttgc cgctatcgct gacttcgaca tggtgcgtaa cgcagtagat     420
gcagctaaag cactgggtat tgatgctcgc gtgggtaacc tgttctccgc tgacctgttc     480
tactctccgg acggcgaaat gttcgacgtg atggaaaaat acggcattct cggcgtggaa     540
atggaagcgg ctggtatcta cggcgtcgct gcagaatttg gcgcgaaagc cctgaccatc     600
tgcaccgtat ctgaccacat ccgcactcac gagcagacca ctgccgctga cgtcagact     660 accttcaacg acatgatcaa atcgcactg gaatccgttc tgctgggcga taaaggtaag     720
cggccgcggg gatcctctag agtcgacctg caggcatgca agcttgggat ctttgtgaag     780
gaaccttact tctgtggtgt gaca                                            804

<210> SEQ ID NO 8
<211> LENGTH: 268
<212> TYPE: PRT
<213> ORGANISM: Trichomonas vaginalis

<400> SEQUENCE: 8

Met Ala Thr Pro His Ile Asn Ala Glu Met Gly Asp Phe Ala Asp Val
1               5                   10                  15

Val Leu Met Pro Gly Asp Pro Leu Arg Ala Lys Tyr Ile Ala Glu Thr
            20                  25                  30

Phe Leu Glu Asp Ala Arg Glu Val Asn Asn Val Arg Gly Met Leu Gly
        35                  40                  45

Phe Thr Gly Thr Tyr Lys Gly Arg Lys Ile Ser Val Met Gly His Gly
    50                  55                  60

Met Gly Ile Pro Ser Cys Ser Ile Tyr Thr Lys Glu Leu Ile Thr Asp
65                  70                  75                  80

Phe Gly Val Lys Lys Ile Ile Arg Val Gly Ser Cys Gly Ala Val Leu
                85                  90                  95

Pro His Val Lys Leu Arg Asp Val Val Ile Gly Met Gly Ala Cys Thr
            100                 105                 110

Asp Ser Lys Val Asn Arg Ile Arg Phe Lys Asp His Asp Phe Ala Ala
        115                 120                 125

Ile Ala Asp Phe Asp Met Val Arg Asn Ala Val Asp Ala Ala Lys Ala
    130                 135                 140

Leu Gly Ile Asp Ala Arg Val Gly Asn Leu Phe Ser Ala Asp Leu Phe
145                 150                 155                 160

Tyr Ser Pro Asp Gly Glu Met Phe Asp Val Met Glu Lys Tyr Gly Ile
                165                 170                 175

Leu Gly Val Glu Met Glu Ala Ala Gly Ile Tyr Gly Val Ala Ala Glu
            180                 185                 190

Phe Gly Ala Lys Ala Leu Thr Ile Cys Thr Val Ser Asp His Ile Arg
```

```
                  195                 200                 205
Thr His Glu Gln Thr Thr Ala Ala Glu Arg Gln Thr Thr Phe Asn Asp
            210                 215                 220

Met Ile Lys Ile Ala Leu Glu Ser Val Leu Leu Gly Asp Lys Gly Lys
225                 230                 235                 240

Arg Pro Arg Gly Ser Ser Arg Val Asp Leu Gln Ala Cys Lys Leu Gly
                245                 250                 255

Ile Phe Val Lys Glu Pro Tyr Phe Cys Gly Val Thr
            260                 265

<210> SEQ ID NO 9
<211> LENGTH: 2135
<212> TYPE: DNA
<213> ORGANISM: Escherichia coli

<400> SEQUENCE: 9
```

| | | | | | |
|---|---|---|---|---|---|
| tctaggcggc | cgcgatctat | acattgaatc | aatattggca | attagccata | ttagtcattg | 60 |
| gttatatagc | ataaatcaat | attggctatt | ggccattgca | tacgttgtat | ctatatcata | 120 |
| atatgtacat | ttatattggc | tcatgtccaa | tatgaccgcc | atgttgacat | tgattattga | 180 |
| ctagttatta | atagtaatca | attacggggt | cattagttca | tagcccatat | atggagttcc | 240 |
| gcgttacata | acttacggta | aatggcccgc | ctggctgacc | gcccaacgac | ccccgcccat | 300 |
| tgacgtcaat | aatgacgtat | gttcccatag | taacgccaat | agggactttc | cattgacgtc | 360 |
| aatgggtgga | gtatttacgg | taaactgccc | acttggcagt | acatcaagtg | tatcatatgc | 420 |
| caagtccgcc | ccctattgac | gtcaatgacg | gtaaatggcc | cgcctggcat | tatgcccagt | 480 |
| acatgacctt | acgggacttt | cctacttggc | agtacatcta | cgtattagtc | atcgctatta | 540 |
| ccatggtgat | gcggttttgg | cagtacacca | atgggcgtgg | atagcggttt | gactcacggg | 600 |
| gatttccaag | tctccacccc | attgacgtca | atgggagttt | gttttggcac | caaaatcaac | 660 |
| gggactttcc | aaaatgtcgt | aataaccccg | ccccgttgac | gcaaatgggc | ggtaggcgtg | 720 |
| tacggtggga | ggtctatata | agcagagctc | gtttagtgaa | ccgtcagatc | cggtcgcgcg | 780 |
| aattcgagct | cggtacccgg | ggatccggtg | gtggtgcaaa | tcaaagaact | gctcctcagt | 840 |
| ggatgttgcc | tttacttcta | ggcctgtacg | gaagtgttac | ttctgctcta | aaagctgcgg | 900 |
| aattgtaccc | gcggccgcat | ggctaccccca | cacattaatg | cagaaatggg | cgatttcgct | 960 |
| gacgtagttt | tgatgccagg | cgacccgctg | cgtgcgaagt | atattgctga | actttccttt | 1020 |
| gaagatgccc | gtgaagtgaa | caacgttcgc | ggtatgctgg | gcttcaccgg | tacttacaaa | 1080 |
| ggccgcaaaa | tttccgtaat | gggtcacggt | atgggtatcc | cgtcctgctc | catctacacc | 1140 |
| aaagaactga | tcaccgattt | cggcgtgaag | aaaattatcc | gcgtgggttc | ctgtggcgca | 1200 |
| gttctgccgc | acgtaaaact | gcgcgacgtc | gttatcggta | tgggtgcctg | caccgattcc | 1260 |
| aaagttaacc | gcatccgttt | taaagaccat | gactttgccg | ctatcgctga | cttcgacatg | 1320 |
| gtgcgtaacg | cagtagatgc | agctaaagca | ctgggtattg | atgctcgcgt | gggtaacctg | 1380 |
| ttctccgctg | acctgttcta | ctctccggac | ggcgaaatgt | tcgacgtgat | ggaaaaatac | 1440 |
| ggcattctcg | gcgtggaaat | ggaagcggct | ggtatctacg | gcgtcgctgc | agaatttggc | 1500 |
| gcgaaagccc | tgaccatctg | caccgtatct | gaccacatcc | gcactcacga | gcagaccact | 1560 |
| gccgctgagc | gtcagactac | cttcaacgac | atgatcaaaa | tcgcactgga | atccgttctg | 1620 |
| ctgggcgata | aggtaagcg | gccgcgggga | tcctctagag | tcgacctgca | ggcatgcaag | 1680 |
| cttgggatct | ttgtgaagga | accttaactt | ctgtggtgtg | acataattgg | acaaactacc | 1740 |

-continued

```
tacagagatt taaagctcta aggtaaatat aaaattttta agtgtataat gtgttaaact    1800
actgattcta attgtttgtg tattttagat tcacagtccc aaggctcatt tcaggcccct    1860
cagtcctcac agtctgttca tgatcataat cagccatacc acatttgtag aggttttact    1920
tgctttaaaa aacctcccac acctcccct gaacctgaaa cataaaatga atgcaattgt     1980
tgttgttaac ttgtttattg cagcttataa tggttacaaa taaagcaata gcatcacaaa    2040
tttcacaaat aaagcatttt tttcactgca ttctagttgt ggtttgtcca aactcatcaa    2100
tgtatcttat catgtctgga tcgcggccgc ctaga                                2135
```

```
<210> SEQ ID NO 10
<211> LENGTH: 262
<212> TYPE: PRT
<213> ORGANISM: Escherichia coli

<400> SEQUENCE: 10
```

Met Ala Thr Pro His Ile Asn Ala Glu Met Gly Asp Phe Ala Asp Val
1               5                   10                  15

Val Leu Met Pro Gly Asp Pro Leu Arg Ala Lys Tyr Ile Ala Glu Thr
            20                  25                  30

Phe Leu Glu Asp Ala Arg Glu Val Asn Asn Val Arg Gly Met Leu Gly
        35                  40                  45

Phe Thr Gly Thr Tyr Lys Gly Arg Lys Ile Ser Val Met Gly His Gly
    50                  55                  60

Met Gly Ile Pro Ser Cys Ser Ile Tyr Thr Lys Glu Leu Ile Thr Asp
65                  70                  75                  80

Phe Gly Val Lys Lys Ile Ile Arg Val Gly Ser Cys Gly Ala Val Leu
                85                  90                  95

Pro His Val Lys Leu Arg Asp Val Val Ile Gly Met Gly Ala Cys Thr
            100                 105                 110

Asp Ser Lys Val Asn Arg Ile Arg Phe Lys Asp His Asp Phe Ala Ala
        115                 120                 125

Ile Ala Asp Phe Asp Met Val Arg Asn Ala Val Asp Ala Ala Lys Ala
    130                 135                 140

Leu Gly Ile Asp Ala Arg Val Gly Asn Leu Phe Ser Ala Asp Leu Phe
145                 150                 155                 160

Tyr Ser Pro Asp Gly Glu Met Phe Asp Val Met Glu Lys Tyr Gly Ile
                165                 170                 175

Leu Gly Val Glu Met Glu Ala Ala Gly Ile Tyr Gly Val Ala Ala Glu
            180                 185                 190

Phe Gly Ala Lys Ala Leu Thr Ile Cys Thr Val Ser Asp His Ile Arg
        195                 200                 205

Thr His Glu Gln Thr Thr Ala Ala Glu Arg Gln Thr Thr Phe Asn Asp
    210                 215                 220

Met Ile Lys Ile Ala Leu Glu Ser Val Leu Leu Gly Asp Lys Gly Lys
225                 230                 235                 240

Arg Pro Arg Gly Ser Ser Arg Val Asp Leu Gln Ala Cys Lys Leu Gly
                245                 250                 255

Ile Phe Val Lys Glu Pro
            260

```
<210> SEQ ID NO 11
<211> LENGTH: 801
<212> TYPE: DNA
<213> ORGANISM: Trichomonas vaginalis

<400> SEQUENCE: 11
```

```
atggcaacac cccataactc tgctcaggtt ggcgatttcg ctgaaacagt cctcatgtgc      60
ggtgatccac tccgcgctaa gctcattgct gagacatatc ttgaaaatcc aaagcttgtc     120
aacaatgttc gtggcattca aggctacacc ggcacataca agggaaagcc aatctctgtc     180
atgggccatg gtatgggctt gccatcaatc tgcatctatg cagaggagct ttactccaca     240
tacaaggtca agacaatcat ccgtgttggt acatgcggcg caattgacat ggacatccac     300
acacgcgata tcgttatctt cacctctgct ggtacaaact ccaagatcaa cagaatccgc     360
ttcatggatc acgattatcc agccacagca tctttcgatg ttgtttgcgc cttagttgat     420
gctgctaagg aactcaacat cccagctaag gtcggtaagg gattctcaac agatctcttc     480
tacaatccac aaaccgaact cgcacagctc atgaacaagt tccacttcct cgctgttgaa     540
atggaatctg ctggcctctt cccaattgct gacctttatg gcgcaagagc tggctgcatc     600
tgcacagttt cagatcacat cctccaccat gaagaaacaa cagccgaaga acgccagaac     660
tccttccaaa acatgatgaa gatcgcactt gaagcagcaa tcaaattagg taagcggccg     720
cggggatcct ctagagtcga cctgcaggca tgcaagcttg ggatctttgt gaaggaacct     780
tacttctgtg gtgtgacata a                                               801

<210> SEQ ID NO 12
<211> LENGTH: 266
<212> TYPE: PRT
<213> ORGANISM: Trichomonas vaginalis

<400> SEQUENCE: 12

Met Ala Thr Pro His Asn Ser Ala Gln Val Gly Asp Phe Ala Glu Thr
1               5                   10                  15

Val Leu Met Cys Gly Asp Pro Leu Arg Ala Lys Leu Ile Ala Glu Thr
            20                  25                  30

Tyr Leu Glu Asn Pro Lys Leu Val Asn Asn Val Arg Gly Ile Gln Gly
        35                  40                  45

Tyr Thr Gly Thr Tyr Lys Gly Lys Pro Ile Ser Val Met Gly His Gly
    50                  55                  60

Met Gly Leu Pro Ser Ile Cys Ile Tyr Ala Glu Glu Leu Tyr Ser Thr
65                  70                  75                  80

Tyr Lys Val Lys Thr Ile Ile Arg Val Gly Thr Cys Gly Ala Ile Asp
                85                  90                  95

Met Asp Ile His Thr Arg Asp Ile Val Ile Phe Thr Ser Ala Gly Thr
            100                 105                 110

Asn Ser Lys Ile Asn Arg Ile Arg Phe Met Asp His Asp Tyr Pro Ala
        115                 120                 125

Thr Ala Ser Phe Asp Val Val Cys Ala Leu Val Asp Ala Ala Lys Glu
    130                 135                 140

Leu Asn Ile Pro Ala Lys Val Gly Lys Gly Phe Ser Thr Asp Leu Phe
145                 150                 155                 160

Tyr Asn Pro Gln Thr Glu Leu Ala Gln Leu Met Asn Lys Phe His Phe
                165                 170                 175

Leu Ala Val Glu Met Glu Ser Ala Gly Leu Phe Pro Ile Ala Asp Leu
            180                 185                 190

Tyr Gly Ala Arg Ala Gly Cys Ile Cys Thr Val Ser Asp His Ile Leu
        195                 200                 205

His His Glu Glu Thr Thr Ala Glu Glu Arg Gln Asn Ser Phe Gln Asn
    210                 215                 220

Met Met Lys Ile Ala Leu Glu Ala Ala Ile Lys Leu Gly Lys Arg Pro
```

```
                  225                 230                 235                 240
Arg Gly Ser Ser Arg Val Asp Leu Gln Ala Cys Lys Leu Gly Ile Phe
                245                 250                 255

Val Lys Glu Pro Tyr Phe Cys Gly Val Thr
            260                 265
```